(12) United States Patent
Yamamoto et al.

(10) Patent No.: US 10,232,596 B2
(45) Date of Patent: *Mar. 19, 2019

(54) FIXING DEVICE OF PLURALITY OF SHEETS ASSOCIATED WITH ABSORBENT ARTICLE, AND FIXING METHOD

(71) Applicant: UNICHARM Corporation, Ehime (JP)

(72) Inventors: Hiroki Yamamoto, Kagawa (JP); Yoshihiko Matsumoto, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/306,759

(22) PCT Filed: Jan. 20, 2015

(86) PCT No.: PCT/JP2015/051388
§ 371 (c)(1),
(2) Date: Oct. 25, 2016

(87) PCT Pub. No.: WO2015/166673
PCT Pub. Date: Nov. 5, 2015

(65) Prior Publication Data
US 2017/0050423 A1    Feb. 23, 2017

(30) Foreign Application Priority Data

Apr. 28, 2014   (JP) ................... 2014-092668

(51) Int. Cl.
*B32B 41/00*   (2006.01)
*B32B 37/06*   (2006.01)
(Continued)

(52) U.S. Cl.
CPC .............. *B32B 37/06* (2013.01); *A61F 13/15* (2013.01); *A61F 13/15593* (2013.01);
(Continued)

(58) Field of Classification Search
CPC .......... A61F 13/15707; A61F 13/15764; A61F 13/15699; A61F 13/15634;
(Continued)

(56) References Cited

U.S. PATENT DOCUMENTS 5,162,066 A * 11/1992 Martensson ........... B26D 1/626
156/163
5,224,405 A * 7/1993 Pohjola ............. A61F 13/15756
156/519

(Continued)

FOREIGN PATENT DOCUMENTS

CN    102186673 A    9/2011
JP    7-213554 A    8/1995
(Continued)

OTHER PUBLICATIONS

International Search Report in PCT Application No. PCT/JP2015/051388, dated Apr. 28, 2015.

(Continued)

*Primary Examiner* — Michael N Orlando
*Assistant Examiner* — Joshel Rivera
(74) *Attorney, Agent, or Firm* — Hauptman Ham, LLP

(57) ABSTRACT

A fixing device for fixing an elastic sheet and a low-stretchable sheet via fixing parts while superposing the sheets in a thickness direction includes: a rotating member including protrusions on an outer peripheral surface to form the fixing parts and rotatable along a transport direction; and a sandwiching member arranged at a predetermined position of the rotating member in a rotational direction, and sandwiching the sheets by a surface portion in cooperation with each of the protrusions to form the fixing parts when each of the protrusions passes through the predetermined position, the surface portion being larger than a top surface of each of the protrusions. At a sandwiching position in which the (Continued)

sheets are sandwiched cooperatively by the sandwiching member and the rotating member, the low-stretchable sheet is located between the elastic sheet and the top surface of each of the protrusions of the rotating member.

9 Claims, 12 Drawing Sheets

(51) Int. Cl.
*A61F 13/49* (2006.01)
*A61F 13/15* (2006.01)
*B32B 25/08* (2006.01)
*B29L 31/48* (2006.01)
*B29C 65/08* (2006.01)
*B29C 65/00* (2006.01)

(52) U.S. Cl.
CPC .. *A61F 13/15634* (2013.01); *A61F 13/15699* (2013.01); *A61F 13/15707* (2013.01); *A61F 13/15739* (2013.01); *A61F 13/15764* (2013.01); *A61F 13/49* (2013.01); *B32B 25/08* (2013.01); *B29C 65/086* (2013.01); *B29C 65/087* (2013.01); *B29C 66/1122* (2013.01); *B29C 66/41* (2013.01); *B29C 66/71* (2013.01); *B29C 66/7294* (2013.01); *B29C 66/81433* (2013.01); *B29C 66/8242* (2013.01); *B29C 66/83411* (2013.01); *B29C 66/83413* (2013.01); *B29C 66/83415* (2013.01); *B29C 66/83511* (2013.01); *B29L 2031/4878* (2013.01); *B32B 2307/51* (2013.01); *B32B 2307/726* (2013.01); *B32B 2555/02* (2013.01)

(58) Field of Classification Search
CPC .......... A61F 13/15593; A61F 13/15739; A61F 13/49; A61F 13/15; B32B 37/06; B32B 25/08; B32B 2307/51; B32B 2555/02; B32B 2307/726
USPC ............................ 156/64, 350, 351, 378.379
See application file for complete search history.

(56) References Cited

U.S. PATENT DOCUMENTS

| 5,766,389 A | * | 6/1998 | Brandon | ................. A61F 13/15 |
| | | | | 156/229 |
| 2010/0218881 A1 | * | 9/2010 | Yamamoto | ........ A61F 13/15739 |
| | | | | 156/73.1 |

FOREIGN PATENT DOCUMENTS

| JP | 2007-105453 A | 4/2007 |
| JP | 5124188 B | 1/2013 |
| JP | 2014-014449 A | 1/2014 |
| JP | 2014-54274 | 3/2014 |
| JP | 2014-54274 A | 3/2014 |
| WO | 2008/041639 A1 | 4/2008 |

OTHER PUBLICATIONS

Written Opinion in PCT Application No. PCT/JP2015/051388, dated Apr. 28, 2015.
Office Action in EP Application No. 15786111.3, dated May 26, 2017.
Office Action in CN Application No. 201580022833.0, dated Jul. 6, 2017.
Office Action in EP Application No. 15786111.3, dated Apr. 25, 2018, 3pp.

* cited by examiner

ENLARGED VIEW ALONG ARROWS B-B

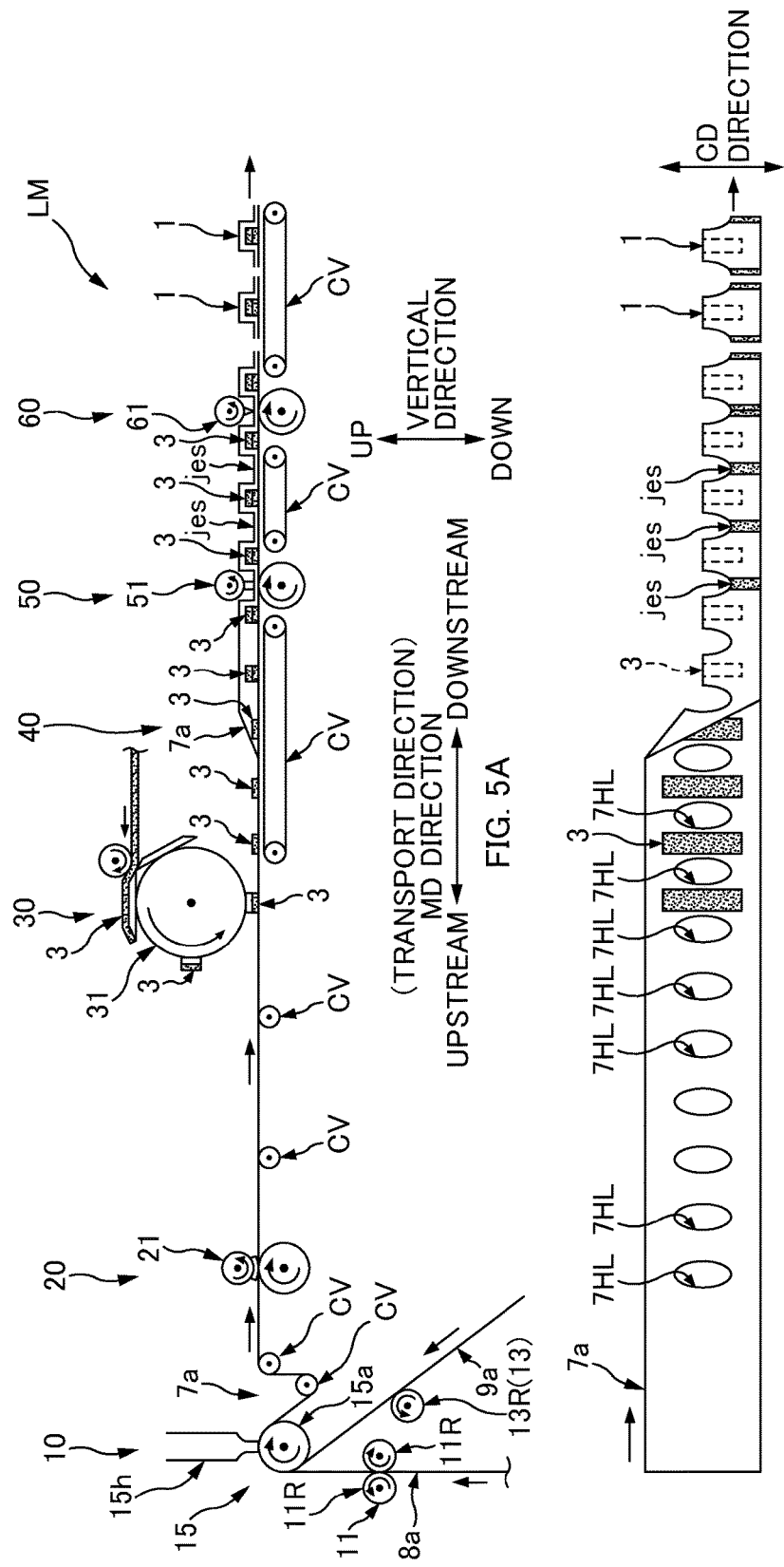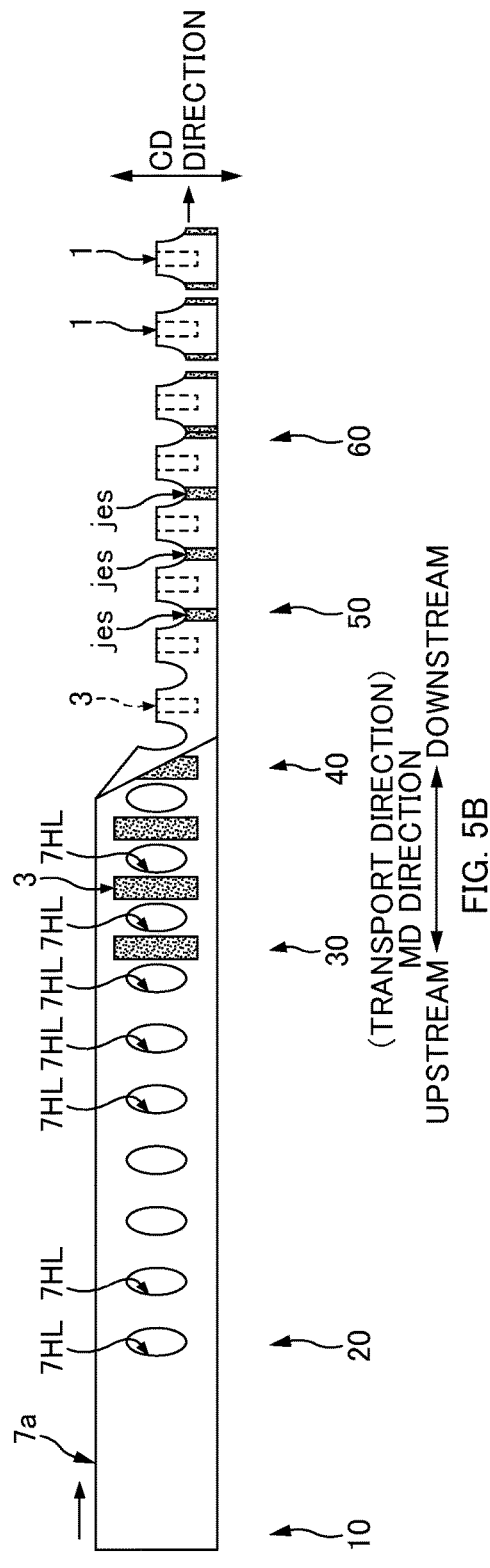

FIXING DEVICE OF PLURALITY OF SHEETS ASSOCIATED WITH ABSORBENT ARTICLE, AND FIXING METHOD

RELATED APPLICATIONS

The present application is a national phase of International Application Number PCT/JP2015/051388, filed Jan. 20, 2015, which claims priority to Japanese Application Number 2014-092668, filed Apr. 28, 2014.

TECHNICAL FIELD

The present invention relates to a fixing device of a plurality of sheets associated with absorbent articles such as disposable diapers, and a fixing method.

BACKGROUND ART

Conventionally, in manufacturing lines of absorbent articles such as disposable diapers, generation of a composite sheet is performed by fixing an elastic sheet and a low-stretchable sheet that has lower stretchability than that of the elastic sheet.

CITATION LIST

Patent Literature

[PTL 1] Japanese Patent Application Laid-open Publication No. 2007-105453

SUMMARY OF INVENTION

Technical Problem

The fixation is performed by using such as an ultrasonic welding device 115. FIG. 1A is a schematic side view of a comparative example of the device 115, and FIG. 1B is a schematic enlarged view along arrows B-B of FIG. 1A. The device 115 includes an anvil roller 115a that rotates along a transport direction of sheets 8a and 9a, and a horn 115h arranged at a predetermined position P115h in a rotational direction of the anvil roller 115a. The horn 115h includes a flat vibrating surface 115hs disposed to face an outer peripheral surface 115as of the anvil roller 115a, and the surface 115hs vibrates in a direction in which the space between the outer peripheral surface 115as and the surface 115hs is expanded or contracted. Further, a plurality of protrusions 115at, 115at . . . is disposed on the outer peripheral surface 115as of the anvil roller 115a at a predetermined arrangement pattern such as a staggered pattern (FIG. 1B). Furthermore, an elastic sheet 8a and a low-stretchable sheet 9a are transported in a state of being superposed with each other at a transport speed (m/min) approximately equal to the peripheral speed (m/min) of the anvil roller 115a. The transport path of these both sheets 8a and 9a includes an arrangement position P115h of the horn 115h, which is the predetermined position P115h described above.

Thus, when both the sheets 8a and 9a pass through the arrangement position P115h described above, both the sheets 8a and 9a are sandwiched between the vibrating surface 115hs of the vibrating horn 115h and each of top surfaces of the plurality of protrusions 115at, 115at . . . of the anvil roller 115a, and at this time, ultrasonic vibration energy is selectively charged into respective sandwiched portions of both the sheets 8a and 9a to melt them, thereby forming welding parts j, j . . . in both the sheets 8a and 9a as a plurality of fixing parts j, j . . . , in a dot pattern corresponding to the arrangement pattern of the protrusions 115at described above. Then, both the sheets 8a and 9a are integrally fixed through these welding parts j, j . . . .

Here, in this comparative example, as illustrated in FIG. 1B, the area of the vibrating surface 115hs of the horn 115h is larger than that of the top surface of each of the protrusions 115at. Further, the elastic sheet 8a is positioned on the anvil roller 115a side including the protrusions 115at, whereas the low-stretchable sheet 9a is positioned on the horn 115h side including the flat vibrating surface 115hs.

However, in the case of the positional relationship described above, the strength of the welding parts j of both the sheets 8a and 9a may be lowered. In other words, the top surface of each of the protrusions 115at of the anvil roller 115a comes into contact with the elastic sheet 8a in this example, and accordingly, a portion of the sheet 8a which comes into contact with the top surface of the protrusion 115at is thinly stretched due to high stretchability of the elastic sheet 8a as illustrated in FIG. 1B. Consequently, the amount of the elastic sheet 8a existing on the top surface of each of the protrusions 115at is reduced, that is, it becomes difficult to leave the sufficient amount of the elastic sheet 8a on the top surface of each of the protrusions 115at. As a result, the strength of the welding part j between the elastic sheet 8a and the low-stretchable sheet 9a may be lowered.

The present invention has been made in view of the above problems, and an object thereof is to suppress the deterioration of the strength of the fixing parts such as welding parts, which may occur when each of the protrusions and the surface portion that is larger than the protrusion sandwich the elastic sheet and the low-stretchable sheet to fix them.

Solution to Problem

An aspect of the invention to achieve the above advantage is, a fixing device of a plurality of sheets associated with an absorbent article, the fixing device fixing an elastic sheet that is transported along a transport direction and a low-stretchable sheet that has lower stretchability than that of the elastic sheet via a plurality of fixing parts while superposing the elastic sheet and the low-stretchable sheet in a thickness direction, the fixing device including:

a rotating member that includes a plurality of protrusions on an outer peripheral surface to form the plurality of fixing parts and rotates along the transport direction; and a sandwiching member that is arranged at a predetermined position of the rotating member in a rotational direction, and sandwiches the elastic sheet and the low-stretchable sheet by a surface portion in cooperation with each of the protrusions to form the fixing parts when each of the protrusions passes through the predetermined position, the surface portion being larger than a top surface of each of the protrusions, at a sandwiching position in which the elastic sheet and the low-stretchable sheet are sandwiched cooperatively by the sandwiching member and the rotating member, the low-stretchable sheet being located between the elastic sheet and the top surface of each of the protrusions of the rotating member.

Further, a fixing method of a plurality of sheets associated with an absorbent article, the method fixing an elastic sheet that is transported along a transport direction and a low-stretchable sheet that has lower stretchability than that of the elastic sheet via a plurality of fixing parts while superposing the elastic sheet and the low-stretchable sheet in a thickness direction, the fixing method including:

rotating, along the transport direction, a rotating member that includes a plurality of protrusions on an outer peripheral surface to form the plurality of fixing parts;

arranging a sandwiching member that includes a surface portion at a predetermined position of the rotating member in a rotational direction, the surface portion being larger than a top surface of each of the protrusions; and forming the fixing parts by sandwiching the elastic sheet and the low-stretchable sheet cooperatively by each of the protrusions and the surface portion of the sandwich member when each of the protrusions passes through the predetermined position of the rotating member in the rotational direction, the low-stretchable sheet being located between the elastic sheet and the top surface of each of the protrusions of the rotating member in forming the fixing parts.

Other features of this invention will become clear from the description in this specification and the attached drawings.

Advantageous Effects of Invention

According to the present invention, it is possible to suppress strength reduction of the fixing parts such as welding parts, which may occur when the elastic sheet and the low-stretchable sheet are sandwiched and fixed between each of the protrusions and the surface portion that is larger than each of the protrusions.

BRIEF DESCRIPTION OF DRAWINGS

FIG. 5A is a schematic side view of a manufacturing line LM that manufactures the diaper 1, and FIG. 5B is a schematic plan view illustrating a state in which the diaper 1 is manufactured.

DESCRIPTION OF EMBODIMENTS

Figure 1A:
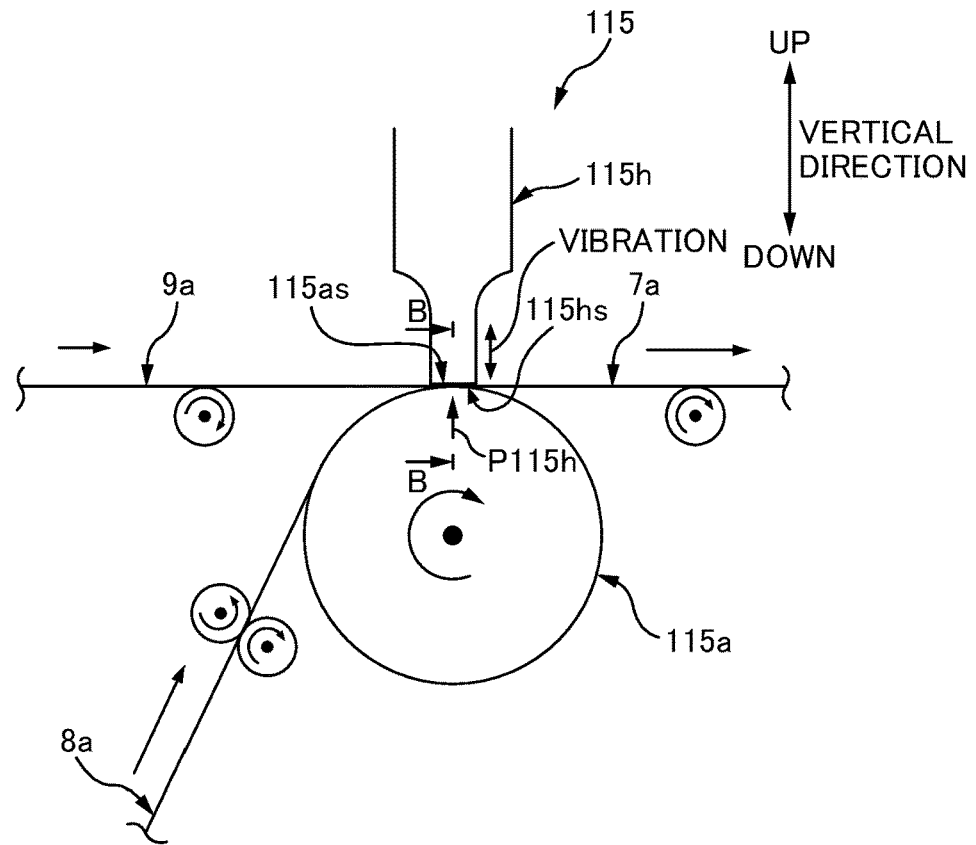
FIG. 1A is a schematic side view of an ultrasonic welding device 115 of a comparative example.
Figure 1B:
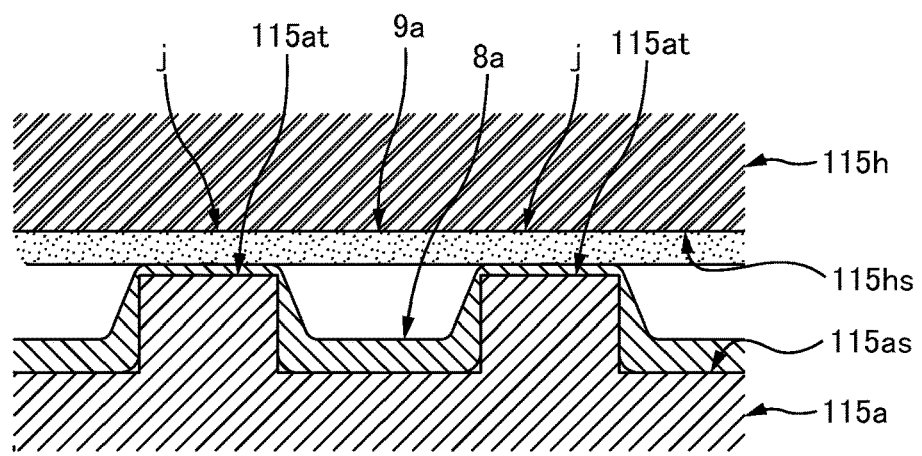
FIG. 1B is a schematic enlarged view along arrows B-B of FIG. 1A.

At least the following matters will become clear with the description of this specification and the attached drawings.

A fixing device of a plurality of sheets associated with an absorbent article, the fixing device fixing an elastic sheet that is transported along a transport direction and a low-stretchable sheet that has lower stretchability than that of the elastic sheet via a plurality of fixing parts while superposing the elastic sheet and the low-stretchable sheet in a thickness direction, the fixing device including:

a rotating member that includes a plurality of protrusions on an outer peripheral surface to form the plurality of fixing parts and rotates along the transport direction; and a sandwiching member that is arranged at a predetermined position of the rotating member in a rotational direction, and sandwiches the elastic sheet and the low-stretchable sheet by a surface portion in cooperation with each of the protrusions to form the fixing parts when each of the protrusions passes through the predetermined position, the surface portion being larger than a top surface of each of the protrusions, at a sandwiching position in which the elastic sheet and the low-stretchable sheet are sandwiched cooperatively by the sandwiching member and the rotating member, the low-stretchable sheet being located between the elastic sheet and the top surface of each of the protrusions of the rotating member.

According to such a fixing device of a plurality of sheets associated with an absorbent article, it is possible to suppress strength reduction of the fixing parts which may be caused when both the plurality of protrusions and the surface portion being larger than the each of the protrusions sandwich and fix the elastic sheet and the low-stretchable sheet. The details are as follows.

First, since the low-stretchable sheet is located between the elastic sheet and the top surface of each of the protrusions of the rotating member, each of the protrusions presses the elastic sheet via the low-stretchable sheet. Thus, the low-stretchable sheet becomes a shock-absorbing material, thereby effectively preventing the elastic sheet from being locally thinly stretched. Further, the aforementioned surface portion that presses the elastic sheet not via the low-stretchable sheet is larger than the top surface of each of the aforementioned protrusions. Accordingly, there is almost no case where the elastic sheet is locally thinly stretched due to the press of the surface portion. Consequently, first, sufficient amount of the elastic sheet can remain on the top surface of each of the protrusions.

On the other hand, the low-stretchable sheet that is located on the protrusion side relative to the elastic sheet has lower elasticity than that of the elastic sheet. Thus, a situation that the low-stretchable sheet is locally thinly stretched due to the press of the top surface of each of the protrusions can be effectively prevented on the basis of the low stretchability of the sheet itself, enabling the sufficient amount of the low-stretchable sheet to remain on the top surface of each of the protrusions. From the above results, the low-stretchable sheet and the elastic sheet can be fixed with a high strength, in other words, strength reduction of the fixing parts of both sheets can be suppressed.

In the fixing device of the plurality of sheets associated with the absorbent article described above, it is preferable that the low-stretchable sheet is wrapped around the protrusion of the outer peripheral surface over an predetermined range of the rotating member in the rotational direction so as to be transported along a transport path that curves in an arc shape along the outer peripheral surface of the rotating member, and the surface portion of the sandwiching member is arranged opposing the outer peripheral surface at the predetermined position included in the predetermined range.

According to such a fixing device of the plurality of sheets associated with the absorbent article, the low-stretchable sheet is wrapped around the protrusions of the outer peripheral surface of the rotating member over the predetermined range in the rotational direction. Thus, a plurality of protrusions, for example, bites into the low-stretchable sheet that is wrapped around the protrusions of the outer peripheral surface, thereby allowing the low-stretchable sheet to be relatively unmovably and firmly held on the rotating member. Consequently, the low-stretchable sheet can be stably transported in the predetermined range described above.

Further, the surface portion is located opposing the aforementioned outer peripheral surface at the predetermined position included in the aforementioned predetermine range. Thus, the elastic sheet is fixed to the low-stretchable sheet when the low-stretchable sheet passes through the predetermined position, and since the predetermined position is included in the aforementioned predetermined range, the transporting state of the low-stretchable sheet is stable. Accordingly, the elastic sheet can be accurately and firmly fixed to the low-stretchable sheet at the predetermined position.

In the fixing device of the plurality of sheets associated with the absorbent article described above, it is preferable that the elastic sheet is wrapped around the protrusion of the outer peripheral surface by being superposed from above the low-stretchable sheet that is wrapped around the protrusion of the outer peripheral surface of the rotating member.

According to such a fixing device of the plurality of sheets associated with the absorbent article, not only the low-stretchable sheet, but also the elastic sheet is wrapped around the protrusions of the outer peripheral surface of the rotating member. Thus, the transport of the elastic sheet is also stabilized, so that the elastic sheet can be accurately and firmly fixed to the low-stretchable sheet.

In the fixing device of the plurality of sheets associated with the absorbent article described above, it is preferable that the surface portion vibrates at a frequency corresponding to ultrasound in a direction in which a space between the outer peripheral surface of the rotating member and the surface portion is expanded or contracted.

According to such a fixing device of the plurality of sheets associated with the absorbent article, the elastic sheet and the low-stretchable sheet are fixed with the ultrasonic welding. That is, a welding part is formed as the fixing part due to the ultrasonic welding. Thus, the elastic sheet and the low-stretchable sheet can be firmly fixed.

In the fixing device of the plurality of sheets associated with the absorbent article described above, it is preferable that the sandwiching member is a second rotating member that rotates so as to send out the elastic sheet and the low-stretchable sheet in the transport direction in cooperation with the rotating member, and the surface portion is provided on an outer peripheral surface of the second rotating member.

According to such a fixing device of the plurality of sheets associated with the absorbent article, the sandwiching member is the second rotatable rotating member, and the aforementioned surface portion is provided on its outer peripheral surface. Accordingly, the surface portion can be provided over the whole periphery of the outer peripheral surface, so that abrasion of the surface portion can be reduced by means of dispersing abrasion of the surface portion. Thus, it is possible to maintain an effect of suppressing the strength reduction of the fixing parts described above over a long period.

In the fixing device of the plurality of sheets associated with the absorbent article described above, it is preferable that the sandwiching member is unrotatably provided along the transport direction, a pressing force in a direction toward the outer peripheral surface of the rotating member is exerted on the sandwiching member, the surface portion of the sandwiching member includes a flat surface opposing the outer peripheral surface, and in a non-rotating state of the rotating member, a center position of the flat surface of the surface portion is located at an upstream side position in the transport direction with respect to a contact position in which a tangent line parallel to the flat surface of the surface portion contacts each of the protrusions of the outer peripheral surface.

According to such a fixing device of the plurality of sheets associated with the absorbent article, the surface portion of the sandwiching member can be effectively prevented from being caught by each of the protrusions of the outer peripheral surface of the rotating member. The details are as follows.

First, the surface portion of the sandwiching member is pressed against the protrusions of the outer peripheral surface of the rotating member through the elastic sheet and the low-stretchable sheet by the aforementioned pressing force. Further, the rotating member rotates while allowing its rotational direction to be along the downstream side in the transport direction. Thus, a sliding force directed to the downstream side in the transport direction is exerted on the surface portion of the sandwiching member, and accordingly, the sandwiching member slightly bends so that the surface portion moves to the downstream side in the transport direction. Then, by the amount of bending, the space between the protrusion of the outer peripheral surface of the rotating member and the surface portion is narrowed, and thus the surface portion is easily caught by the protrusion.

In this regard, according to the structure stated above, the center position of the flat surface of the surface portion is located on the upstream side in the rotational direction relative to the contact position described above in a non-rotating state of the rotating member. Thus, even in a case where the sandwiching member bends and the surface portion slightly moves downstream in the transport direction at the time of rotation of the rotating member, an appropriate space between the protrusion of the outer peripheral surface of the rotating member and the surface portion can be secured, and consequently, it is possible to suppress that the surface portion is caught by the protrusion.

In the fixing device of the plurality of sheets associated with the absorbent article described above, it is preferable that the elastic sheet is a fibrous sheet including a plurality of fibers.

According to such a fixing device of the plurality of sheets associated with the absorbent article, an action effect performed by the present invention, that is, an action effect that suppresses strength reduction of the fixing parts can be further effectively obtained. The details are as follows.

First, the elastic sheet is a fibrous sheet as described above. When fibers included in the sheet are pressed by the top surface of each of the protrusions, the fibers are easily pushed away to sides of the protrusion. Thus, particularly the fibrous sheet becomes easily in a state of being thinly stretched as a whole, so that it is particularly difficult to allow the sufficient amount of the sheet to remain on the top surface of each of the protrusions, and the strength reduction of the fixing parts is easily caused. Accordingly, in the case of the elastic sheet constituted by the fibrous sheet, an effect of suppressing the strength reduction of the fixing parts, which is an action effect of the present invention described above, can be obtained effectively by the amount that is less likely to remain on the top surface of the protrusion.

Moreover, a fixing method of a plurality of sheets associated with an absorbent article, the method fixing an elastic sheet that is transported along a transport direction and a low-stretchable sheet that has lower stretchability than that of the elastic sheet via a plurality of fixing parts while superposing the elastic sheet and the low-stretchable sheet in a thickness direction, the fixing method including:

rotating, along the transport direction, a rotating member that includes a plurality of protrusions on an outer peripheral surface to form the plurality of fixing parts;

arranging a sandwiching member that includes a surface portion at a predetermined position of the rotating member in a rotational direction, the surface portion being larger than a top surface of each of the protrusions; and forming the fixing parts by sandwiching the elastic sheet and the low-stretchable sheet cooperatively by each of the protrusions and the surface portion of the sandwich member when each of the protrusions passes through the predetermined position of the rotating member in the rotational direction, the low-stretchable sheet being located between the elastic sheet and the top surface of each of the protrusions of the rotating member in forming the fixing parts.

According to such a fixing method of the plurality of sheets associated with the absorbent article, it is possible to suppress the strength reduction of the fixing parts of the low-stretchable sheet and the elastic sheet depending on the same theory as that described in the aforementioned fixing device.

Present Embodiment

A fixing device 15 of sheets 8a and 9a associated with an absorbent article of the present embodiment is used in a manufacturing line LM of a pants-type disposable diaper 1 which is an example of an absorbent article.

Figure 2A:
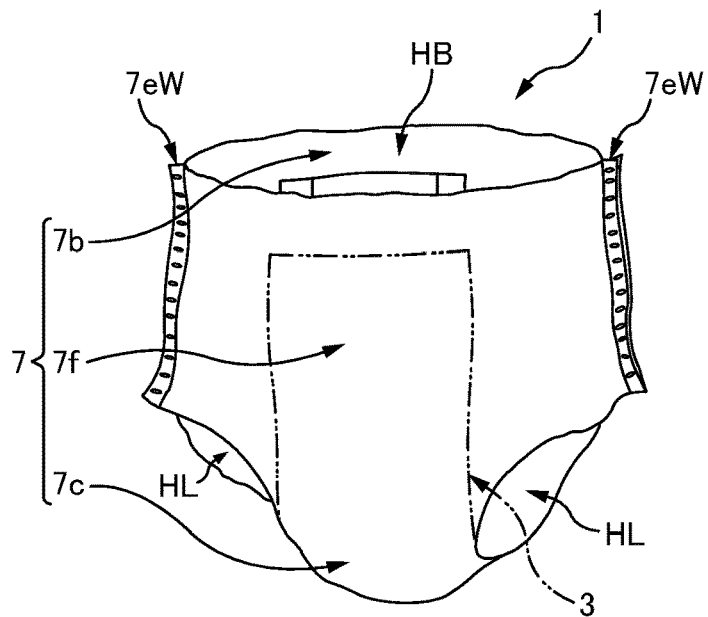
FIG. 2A is a schematic perspective view of a pants-type diaper 1 as an example of an absorbent article associated with the present embodiment.
Figure 2B:
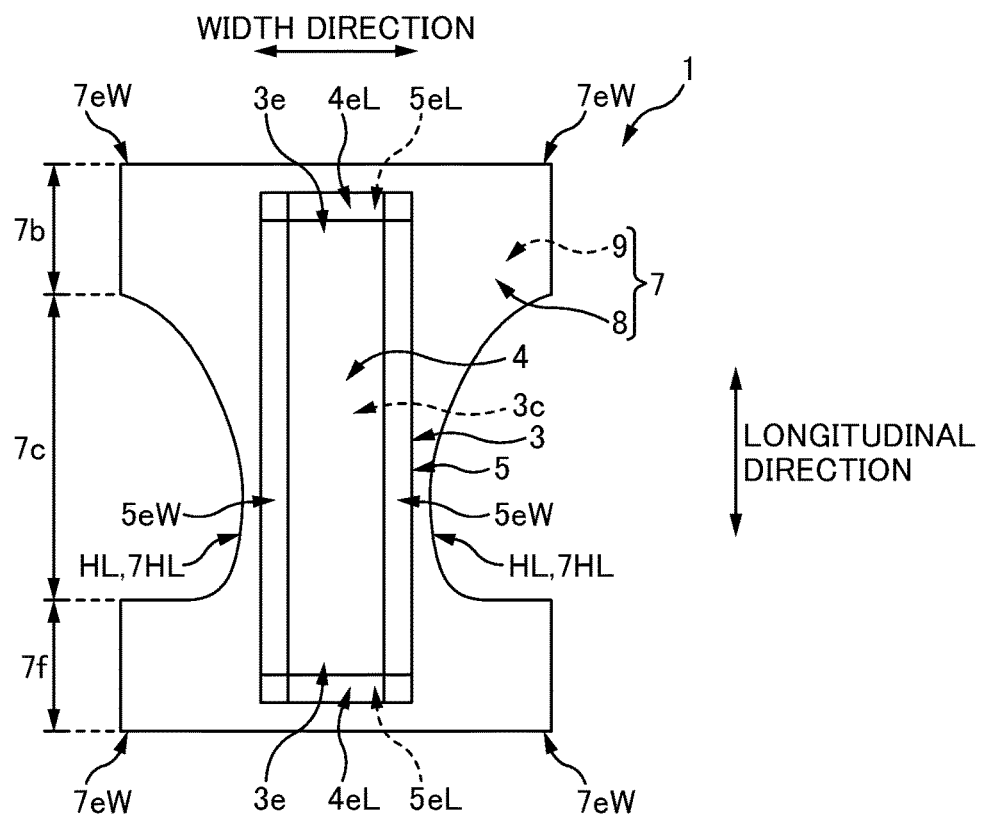
FIG. 2B is a schematic plan view of the diaper 1 in a developed state when seen from a skin side.
Figure 3:
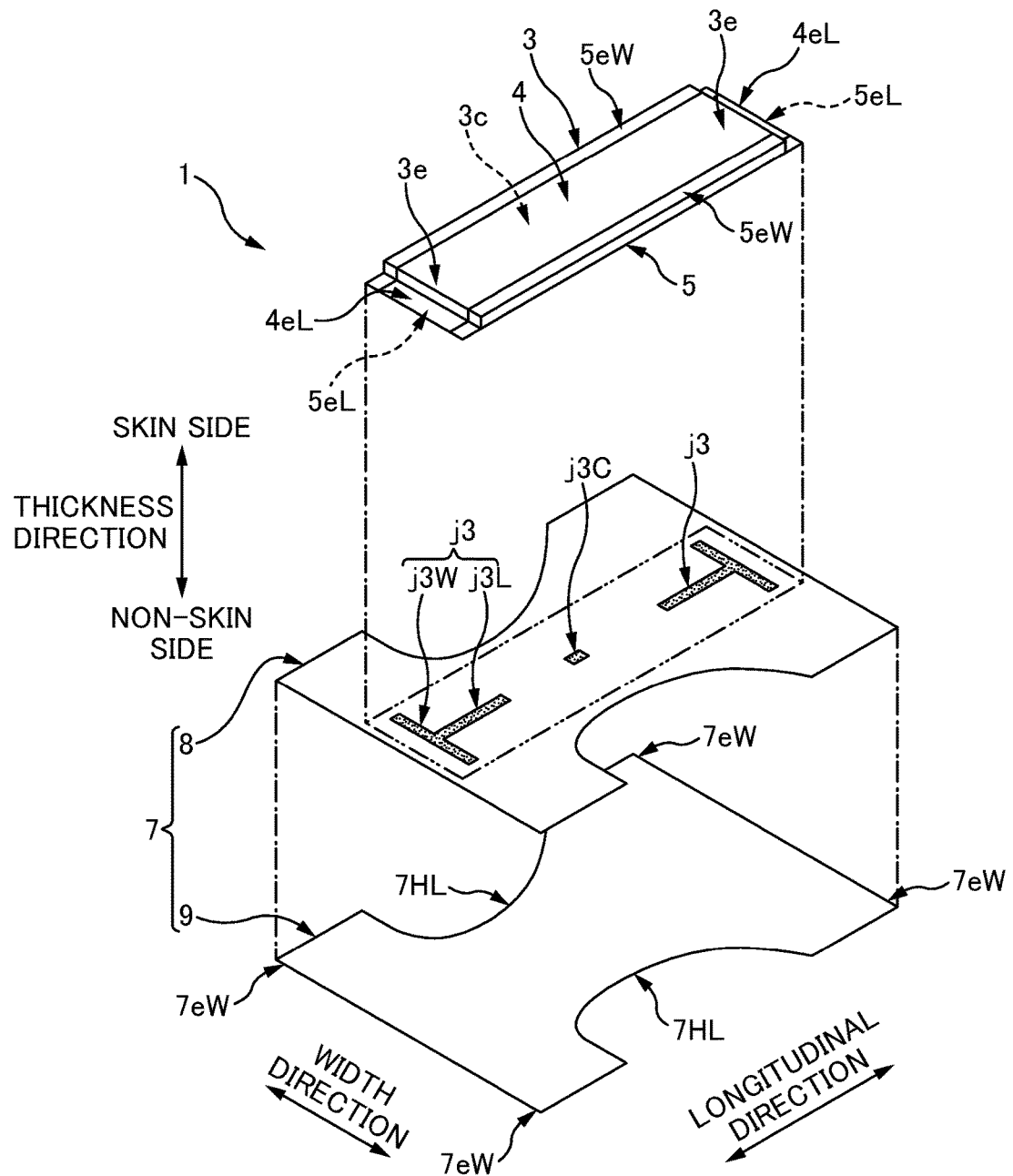
FIG. 3 is a schematic perspective view illustrating the divided diaper 1 in the developed state.

FIG. 2A is a schematic perspective view of the pants-type diaper 1. FIG. 2B is a schematic plan view when the diaper 1 in a developed state is seen from a skin side. FIG. 3 is a schematic perspective view illustrating the divided diaper 1 in a developed state.

Note that, in the description below, when the diaper 1 is worn by the wearer, a side to be located on a skin side of the wearer is merely referred to as a "skin side", whereas a side to be located on a non-skin side of the wearer is merely referred to as a "non-skin side".

As illustrated in FIG. 2B and FIG. 3, this diaper 1 is, for example a two-piece type diaper 1. In other words, the diaper 1 includes an absorbent main body 3, as a first component, that has such as a substantially rectangular shape when seen in a planar view and absorbs excreted liquid such as urine, and an exterior sheet 7, as a second component, that has a substantially hourglass shape when seen in a planar view and is provided to cover the non-skin side surface of the aforementioned absorbent main body 3 and constitute an exterior of the diaper 1.

As illustrated in FIG. 3, the absorbent main body 3 includes an absorbent core 3c that absorbs the excreted liquid. The absorbent core 3c is produced by forming liquid absorbent fiber such as pulp fibers and liquid absorbent particles such as high-absorbent polymer into a substantially rectangular shape when seen in a planer view as an example of a predetermined shape. Note that, the absorbent core 3c described above may be covered by a liquid-permeable covering sheet such as tissue paper as necessary.

On the skin side surface of the absorbent core 3c, a liquid permeable top sheet 4 such as nonwoven fabric is provided so as to cover the surface, and similarly, on the non-skin side surface of the absorbent core 3c, a liquid non-permeable leak-proof sheet 5 such as a film is provided so as to entirely cover the surface.

Here, in this example, both sheets 4 and 5 are formed into a substantially rectangular shape when seen in a planer view, and also both sheets 4 and 5 project outward from each of end portions of the absorbent core 3c in the longitudinal direction. Then, a projected portion 4eL of the top sheet 4 and a projected portion 5eL of the leak-proof sheet 5 are joined with each other by bonding, welding and the like. Further, with respect to the width direction, only the leak-proof sheet 5 is sized to project outward from both sides of the absorbent core 3c, and these projected portions 5eW, 5eW are each folded back to the skin side to be fixed by bonding, welding and the like in a state of covering each end portion of the top sheet 4 in the width direction. Accordingly, the absorbent core 3c is made into a state of being wrapped with the top sheet 4 and the leak-proof sheet 5, thereby forming a shape of the absorbent main body 3.

The exterior sheet 7 is a soft sheet having a substantially hourglass shape when seen in a planar view, and includes a thickness direction, a longitudinal direction and a width direction as the three directions which intersect one another in a developed state of FIG. 2B. Further, the exterior sheet 7 is divided into three portions 7f, 7b and 7c with respect to the longitudinal direction. That is, the exterior sheet 7 is divided into an abdomen side part 7f disposed on the abdomen side of the wearer, a back side part 7b disposed on the back side of the wearer, and a crotch part 7c disposed on the crotch of the wearer. Naturally, the crotch part 7c is located between the abdomen side part 7f and the back side part 7b, so that the crotch part 7c is a portion 7c having a constricted shape in the width direction in the substantially hourglass shape when seen in a planar view.

As illustrated in FIG. 3, a so-called laminate sheet 7 having a two-layer structure is used for the exterior sheet 7. That is, the exterior sheet 7 includes an inner layer sheet 8 that is directed to the skin side of the wearer and constitutes an inner layer when the diaper 1 is worn and an outer layer sheet 9 that is directed to the non-skin side and constitutes an outer layer when the diaper 1 is worn, and the inner layer sheet 8 and the outer layer sheet 9 are superposed in the thickness direction and joined by bonding, welding and the like. Note that, in this example, the welding is performed in a predetermined joining pattern made by non-continuously distributing joined parts j, j . . . which are parts that have been joined. That is, welding parts j, j . . . are formed as the joined parts j, j . . . .

Figure 4:
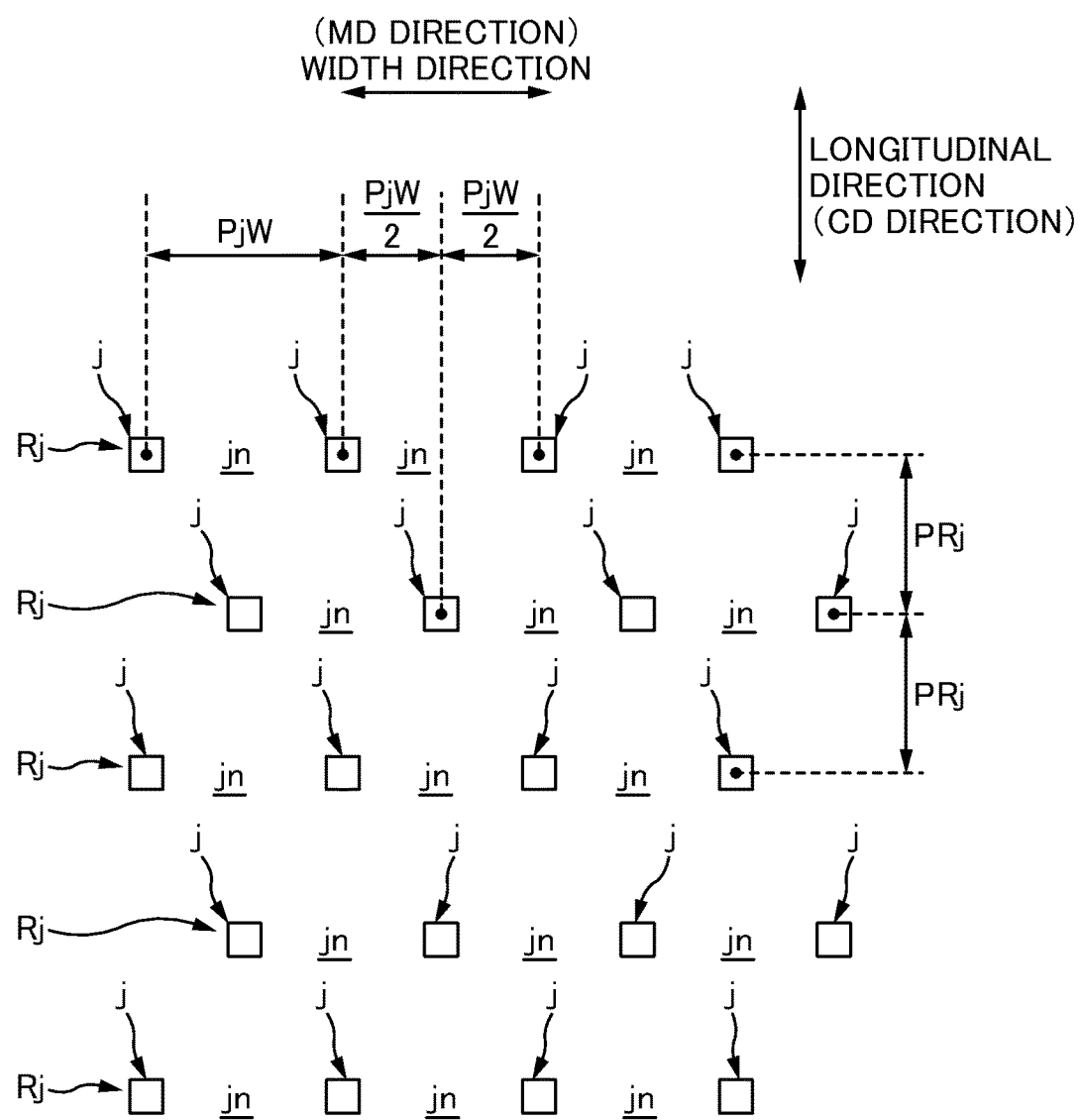
FIG. 4 is a schematic enlarged view of a joining pattern of an inner layer sheet 8 and an outer layer sheet 9.

FIG. 4 shows a schematic enlarged view of this joining pattern, and in this example, a plurality of joined parts j, j . . . is arranged in a so-called staggered pattern. That is, in the staggered pattern, a plurality of joined part lines Rj is included in which the plurality of joined parts j, j . . . is arranged at a predetermined pitch PjW in the width direction at intervals in the width direction, and the plurality of joined part lines Rj, Rj . . . is each displaced only by a half pitch (=PjW/2) in the width direction between the joined part lines Rj adjacent to one another in the longitudinal direction.

Here, an arbitrary value of the pitch PjW described above is selected, for example, from a range of 2 mm to 7 mm, preferably selected from a range of 3 mm to 5 mm, and further preferably selected from a range of 3.5 mm to 4.5 mm. Further, In FIG. 4, a plurality of joined part lines Rj, Rj . . . is arranged at a predetermined pitch PRj in the longitudinal direction described above. The arbitrary value of the pitch PRj is selected, for example, from a range of 1.5 mm to 5 mm, preferably selected from a range of 2 mm to 4 mm, and further preferably selected from a range of 2 mm to 3 mm. Then, if both the pitch PjW and the pitch PRj are in the respective ranges described above, a non-joined part jn having a proper size can be ensured between the adjacent joined parts j, j, to rapidly form wrinkles described above in the non-joined part jn, and the fixation of the elastic sheet 8a and the low-stretchable sheet 9a can also be appropriately performed.

The elastic sheet 8 having elasticity in the width direction of the diaper 1 is used for a material of the inner layer sheet 8, while the low-stretchable sheet 9 having low stretchability in the width direction of the diaper 1 is used for a material of the outer layer sheet 9. Then, the elastic inner layer sheet 8 in a state of being stretched to a predetermined stretch magnification such as 2.5 times of the natural length in the width direction (hereinafter, referred to as a stretched state) is superposed on the low-stretchable outer layer sheet 9 in a state of being strained in the width direction as well, and both sheets 8 and 9 are integrally fixed in the joining pattern described above.

Thus, when the stretched state described above is released, the inner layer sheet 8 contracts in the width direction of the diaper 1 due to its elasticity. However, at this time, the low-stretchable outer layer sheet 9 is folded into a number of wrinkle-like folds in the width direction of the diaper 1, so that the outer layer sheet 9 quickly follows the contraction of the inner layer sheet 8, thereby shortening the entire length of the sheet 9 in the width direction. Consequently, in an unloaded state in which no external force is exerted on the diaper 1, the exterior sheet 7 is shortened in the width direction as a whole, and the outer surface of the exterior sheet 7 is in a state in which a plurality of wrinkles occurs due to the aforementioned folds of the outer layer sheet 9. However, when the external tensile force in the width direction is exerted to the exterior sheet 7, the exterior sheet 7 can substantially elastically stretch until the wrinkles described above are fully stretched, and thus the exterior sheet 7 of the diaper 1 has a specification having elasticity in the width direction.

The "elasticity" referred in this specification is a property in which when the external tensile force is exerted, a stretch occurs substantially elastically in an acting direction of the external force, and when the external force is released, contraction occurs substantially elastically. Again, the sheet having such elasticity is the "elastic sheet 8" described above.

The elastic sheet 8 preferably satisfies the following conditions. That is, in a state in which both end portions of a band-like sheet in the longitudinal direction having a size of 25 mm in the lateral direction are equally held in whole length of 25 mm in the aforementioned lateral direction respectively, it is preferable that a stretch rate (%) is an arbitrary value in a range of 50% to 300% when the elastic sheet 8 is pulled by the external force of 1.0 (N) in the longitudinal direction using the both end portions as a point of force respectively, and residual stretching strain (%), which remains without contraction after the aforementioned external force is released and contraction occurs, is an arbitrary value in a range of 0% to 40%. Moreover, it is further preferable that, the aforementioned stretch rate is an arbitrary value in a range of 70% to 200%, and the residual stretching strain is an arbitrary value in a range of 0% to 30%. Incidentally, the aforementioned stretch rate (%) is a percentage value of a divided value (=$\Delta$L1/L0) obtained by dividing, by the natural length L0, a subtraction value $\Delta$L1 (=L1−L0) obtained by subtracting the natural length L0 that is a length of the band-like member in the unloaded state before being pulled, from a length L1 of the band-like sheet when being pulled by the external force of 1.0 (N). Further, the aforementioned residual stretching strain (%) is a percentage value of a divided value (=$\Delta$L2/$\Delta$L1) obtained by dividing a subtraction value $\Delta$L2 (=L2−L0) obtained by subtracting the aforementioned natural length L0 before being pulled from the length 2 after the aforementioned external force of 1.0 (N) is released, by a subtraction value $\Delta$L1 (=L1−L0) obtained by subtracting the aforementioned natural length L0 from the length L1 when being pulled by the aforementioned external force.

Further, the "low-stretchable sheet 9" is a sheet having lower stretchability than that of the elastic sheet 8. That is, the "low-stretchable sheet 9" is a sheet in which the stretch rate (%) when the external tensile force of a predetermine magnitude is exerted is lower than the stretch rate (%) of the aforementioned elastic sheet 8. Note that, the low-stretchable sheet 9 preferably satisfies the following conditions. That is, in a state in which both end portions of the band-like sheet in the longitudinal direction having a size of 25 mm in the lateral direction are equally held in whole length of 25 mm in the aforementioned lateral direction respectively, it is preferable that the stretch rate (%) is an arbitrary value in a range of 0% to 20% when the low-stretchable sheet 9 is pulled by the external force of 1.0 (N) in the longitudinal direction using the both end portions as a point of force respectively. Further, it is further preferable that, the aforementioned stretch rate is an arbitrary value in a range of 0% to 10%.

Note that, any of nonwoven fabric, woven fabric, and a film may be employed as the form of the elastic sheet 8 and the low-stretchable sheet 9.

For concrete examples of the nonwoven fabric that can be used for the elastic sheet 8, nonwoven fabric can be exemplified in which appropriate drawing treatment such as gear drawing treatment has been performed to the nonwoven fabric that includes thermoplastic elastomer fiber substantially exhibiting elasticity and thermoplastic resin fiber substantially exhibiting non-elasticity. In other words, by performing such drawing treatment, substantially non-elastic thermoplastic resin fiber included in the nonwoven fabric is subjected to plastic deformation, and the joined point of the mutual fibers is broken or the like, so that the nonwoven fabric can be changed into a configuration in which a substantially elastic stretching/contracting deformation of the thermoplastic elastomer fiber is less likely to be impaired, thereby developing elasticity of the nonwoven fabric and bringing it into a usable state as an elastic sheet 8.

Note that, as a substantially elastic thermoplastic elastomer, polyurethane-based elastomer, polystyrene-based elastomer, polyolefin-based elastomer, polyamide-based elastomer and the like can be exemplified. Further, as substantially non-elastic thermoplastic resin fiber, fiber containing a polyolefin-based resin and the like can be exemplified. Furthermore, as a polyolefin-based resin, polyethylene (PE), polypropylene (PP), ethylene/alpha-olefin copolymer and the like can be exemplified. Note that, in this example, a mixed type of nonwoven fabric containing polyurethane-based elastomer fiber and PP fiber, to which the gear drawing treatment is performed, is used as the elastic sheet 8.

Moreover, for concrete examples of the nonwoven fabric that can be used for the low-stretchable sheet 9, spunbond nonwoven fabric constituted by fibers such as PE, PP, polyester, and polyamide, meltblown nonwoven fabric, so-called SMS nonwoven fabric constituted by layering spunbond nonwoven fabric, meltblown nonwoven fabric and spunbond nonwoven fabric, air-through nonwoven fabric and the like can be exemplified. Note that, the structure of fibers is not limited to a single fiber made of a single thermoplastic resin as described above. For example, a composite fiber having a core-sheath structure in which a core material is PP and a sheath material is PE may be used, and a fiber having a structure other than those may be employed. Note that, in this example, the spunbond nonwoven fabric of PP fiber is used as the low-stretchable sheet 9.

As illustrated in FIG. 2B and FIG. 3, at the center position in the width direction of the skin side surface of such an exterior sheet 7 having a two-layer structure, that is, the skin side surface of the inner layer sheet 8, the absorbent main body 3 described above is attached in a state of aligning the mutual longitudinal directions. The attachment is performed by allowing at least each of end portions 3e, 3e of the absorbent main body 3 in the longitudinal direction to be joined to the exterior sheet 7. In this example, as illustrated in FIG. 3, joined parts j3, j3 that join the absorbent main body 3 and the exterior sheet 7 are respectively formed into a substantially T-shaped in each of the end portions 3e, 3e. In other words, each of the joined parts j3, j3 includes a laterally long band-like portion j3w that is long in the width direction of the diaper 1, and a longitudinal band-like portion j3L that extends toward the crotch part 7c with a center portion of the laterally long band-like portion j3w in the width direction described above as a starting point. Accordingly, the absorbent main body 3 and the exterior sheet 7 are effectively prevented from being mutually restrained more than required. However, the shape of the joined part j3 is not limited thereto. For example, a dot-like joined part j3C may be additionally arranged at a position between a pair of T-shaped joined parts j3, j3, or a joined part (not shown) having a substantially rectangular shape and an extent over the substantially entire region of the respective end portions 3e, 3e of the absorbent main body 3 may be formed in each of the end portions 3e, 3e. In addition, a joined part having a shape other than the shape described above may be formed. Moreover, in this example, forming the joined part j3 is achieved by bonding it with hot-melt adhesive. However, this invention is not limited thereto, and for example, welding may also be employed.

Then, the exterior sheet 7 to which the absorbent main body 3 has been attached as shown in FIG. 2B is folded in two at the crotch part 7c so that the abdomen side part 7f and the back side part 7b are superposed. Then, in this superposed state, the abdomen side part 7f and the back side part 7b are joined at each of end portions 7eW in the width direction, thereby forming a shape of the pants-type diaper 1 in which a waist opening portion HB and a pair of leg-surrounding opening portions HL, HL are formed as shown in FIG. 2A.

FIG. 5A is a schematic side view of the manufacturing line LM that manufactures the diaper 1. Further, FIG. 5B illustrates a state in which the diaper 1 is manufactured in correspondence with FIG. 5A in a schematic plan view.

In this manufacturing line LM, a base material sheet 7a of the diaper 1 is produced first. Then, the base material sheet 7a is continuously transported along the predetermined transport direction by appropriate transport mechanisms CV, CV . . . and the like. Then, during the transportation, various processing such as punching and attachment of components are performed to the base material sheet 7a, and the form of the base material sheet 7a is sequentially changed each time, thereby finally manufacturing the diaper 1 in a state of FIG. 2A. Note that, as illustrated in FIG. 5B, in this example, the base material sheet 7a is essentially transported by a so-called lateral flow mode. That is, the base material sheet 7a is transported in a state in which the direction corresponding to the width direction of the diaper 1 is adjusted to the transport direction and the portions that are to be respective diapers 1 are arranged in a line in the transport direction.

As the transport mechanism CV serving for the transportation described above, for example, a transport roller, a suction belt conveyor having a suction holding function on a belt surface that is a placement surface, a belt conveyor having a transport path of the base material sheet 7a which passes through between a pair of endless belts disposed vertically, and the like are utilized.

In the manufacturing line LM, a plurality of processing sections 10, 20 . . . is arranged side by side in the transport direction to perform the various processing described above. In this example, as a plurality of processing sections 10, 20 . . . , an exterior sheet generation processing section 10, a leg-surrounding opening portion forming processing section 20, an absorbent main body attachment processing section 30, a twofold processing section 40, an end seal processing section 50, and a separation processing section 60 are included.

Note that, in the description below, the aforementioned transport direction set on the manufacturing line LM is referred to as an "MD direction". Further, one of the two directions perpendicular to the MD direction is referred to as a "CD direction", and another thereof is referred to as a "Z direction". Note that, the CD direction is parallel to the width direction of the base material sheet 7a, and is directed to a direction perpendicular to the paper surface in FIG. 5A. Further, the Z direction is parallel to the thickness direction of the base material sheet 7a.

Figure 6A:
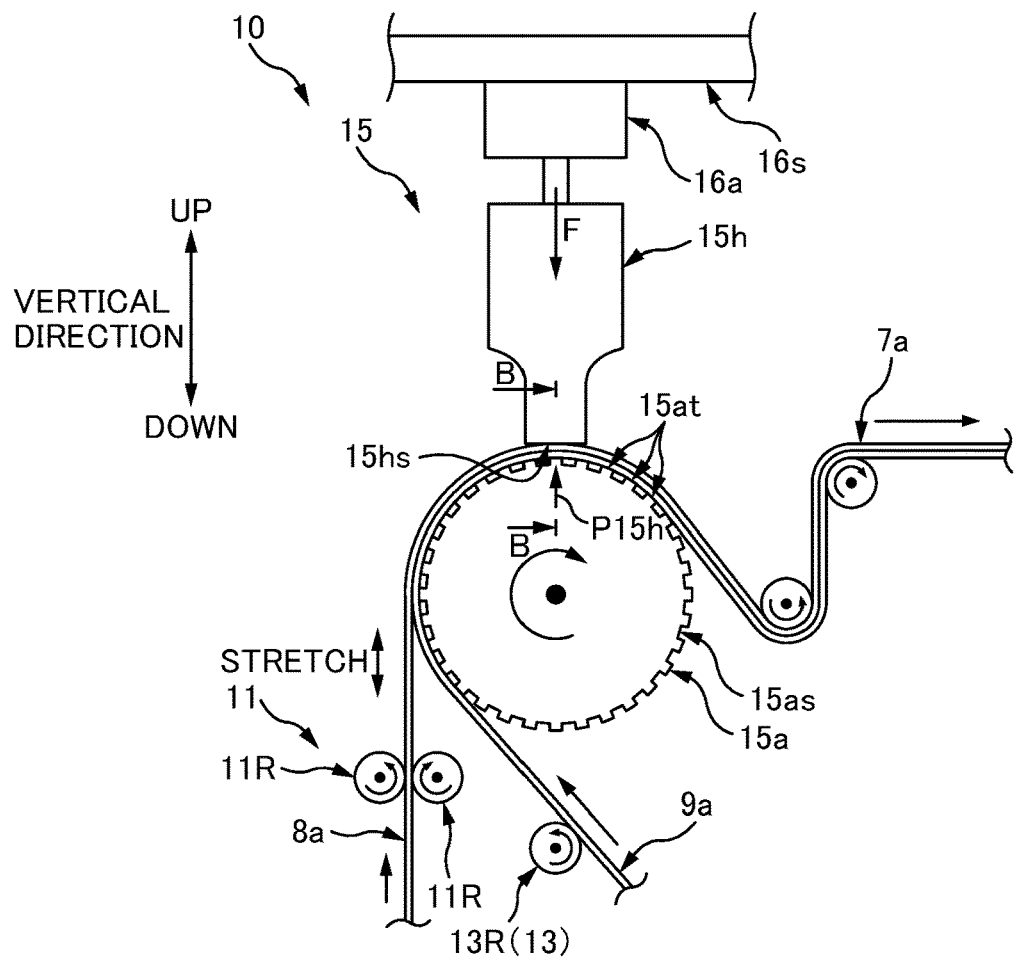
FIG. 6A is a schematic side view of an exterior sheet generation processing section 10.
Figure 6B:
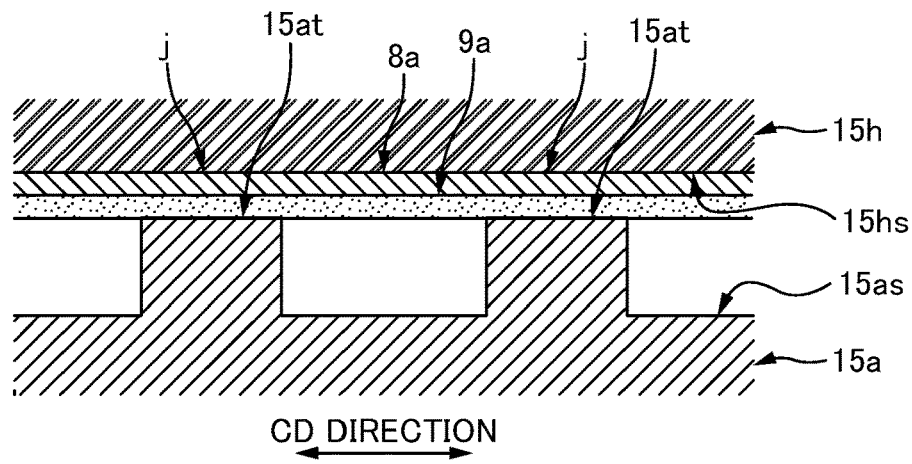
FIG. 6B is a schematic enlarged view along arrows B-B of FIG. 6A.

The fixing device 15 of the sheets 8a and 9a associated with the present embodiment is used in the exterior sheet generation processing section 10. FIG. 6A is a schematic side view of the processing section 10, and FIG. 6B is a schematic enlarged view along arrows B-B of FIG. 6A.

In this exterior sheet generation processing section 10, as the base material sheet 7a of the diaper 1, a continuous sheet 7a (hereinafter, merely referred to as an exterior sheet 7a) of the exterior sheet 7 constituted by being continuously arranged in the MD direction is produced. That is, a continuous sheet 8a (hereinafter, merely referred to as a "elastic sheet 8a") of the elastic sheet 8 that is an inner layer sheet 8 to be transported along the MD direction is stretched in the MD direction from the state of the substantially natural length to the predetermined stretch magnification, and this elastic sheet 8a in the stretched state is superposed from the thickness direction on a continuous sheet 9a (hereinafter, merely referred to as a "low-stretchable sheet 9a") of the low-stretchable sheet 9 that is the outer layer sheet 9 in the stretched state, so that they are joined with each other. Accordingly, the exterior sheet 7a is produced as the base material sheet 7a.

As illustrated in FIG. 6A, the exterior sheet generation processing section 10 includes a transport mechanism 11 of the elastic sheet 8a, a transport mechanism 13 of the low-stretchable sheet 9a, and an ultrasonic welding device 15 as a fixing device 15 disposed downstream from the two transport mechanisms 11, 13 in the MD direction.

The transport mechanism 11 of the elastic sheet 8a is, for example, a nip roll mechanism 11. That is, the mechanism 11 includes a pair of nip rolls 11R, 11R that rotates about a rotary shaft along the CD direction. Then, while the elastic sheet 8a that is continuously transported from the upstream steps is sandwiched by the mutual outer peripheral surfaces of the pair of nip rolls 11R, 11R, the nip rolls 11R, 11R are driven to rotate due to a drive force imparted from a servo motor (not shown) as a drive source, thereby sending out the sheet 8a to the ultrasonic welding device 15.

The transport mechanism 13 of the low-stretchable sheet 9a has, for example, a transport roller 13R, as a main body, that rotates about the rotary shaft along the CD direction. Then, while the roller 13R is contacting with the low-stretchable sheet 9a that is continuously transported from the upstream steps on its outer peripheral surface, the roller 13R is driven to rotate due to a drive force imparted from the servo motor (not shown) as a driving source, thereby sending out the low-stretchable sheet 9a to the ultrasonic welding device 15.

The ultrasonic welding device 15 includes an anvil roller 15a (corresponding to a rotating member) that rotates along the MD direction, and a horn 15h (corresponding to a sandwiching member) that is arranged at a predetermined position P15h in the rotational direction of the anvil roller 15a.

The horn 15h is supported so as to be substantially immovably located at the predetermined position P15h by an appropriate support member 16s. Further, the horn 15h includes a flat vibrating surface 15hs (corresponding to a surface portion) that is arranged to be opposed to the outer peripheral surface 15as of the anvil roller 15a. The surface 15hs vibrates in a direction in which the space between the aforementioned outer peripheral surface 15as and the surface 15hs is expanded or contracted. Frequency of the vibration is a predetermined value such as 20 kHz to 35 kHz, and the amplitude is a predetermined value such as 1 micron to 30 microns. Thus, the vibrating surface 15hs ultrasonically vibrates, thereby ultrasonically welding both the sheets 8a and 9a that pass between the surface 15hs and the outer peripheral surface 15as. Incidentally, the generation of the vibration stated above is performed by, for example, inputting electrical signals of the aforementioned frequency to a piezo element of an unshown converter connected to the horn 15h.

The anvil roller 15a is rotatably supported about the rotary shaft along the CD direction by an appropriate support member that is not shown such as a bearing. The roller 15a is driven to rotate due to a drive force imparted from a servomotor (not shown) as a drive source. Further, the low-stretchable sheet 9a that is sent from the aforementioned transport mechanism 13 and the elastic sheet 8a that is sent from the nip roll mechanism 11 are wrapped around the roller 15a over the predetermined range of the roller 15a in the rotational direction substantially without relative sliding. Thus, the anvil roller 15a is driven to rotate, and thus, both the elastic sheet 8a and the low-stretchable sheet 9a are transported along the outer peripheral surface 15as of the roller 15a at a transport speed V8a9a that is equal to a peripheral speed V15a of the anvil roller 15a. That is, both the sheets 8a and 9a are transported along the transport path that curves along the outer peripheral surface 15as.

Here, the transport speed V8a9a is almost the same value as a peripheral speed V13R of the transport roller 13R for the low-stretchable sheet 9a. Thus, the low-stretchable sheet 9a wraps around the anvil roller 15a substantially without stretching and also in a strained state enough not to be sagged. On the other hand, the transport speed V8a9a is a magnitude obtained by multiplying the peripheral speed V11R of the nip roll 11R in the aforementioned nip roll mechanism 11 by the stretch magnification. Thus, the elastic sheet 8a is stretched up to the aforementioned stretch magnification while passing between the nip roll mechanism 11 and the anvil roller 15a, and wraps around the anvil roller 15a from above the low-elastic sheet 8a in this stretched state. Consequently, the low-stretchable sheet 9a that has been made into a strained state and the elastic sheet 8a that has been stretched up to the stretch magnification are superposed each other in the thickness direction on the outer peripheral surface 15as of the anvil roller 15a.

Further, when both the sheets 8a and 9a in the superposed state pass through the arrangement position P15h of the horn 15h due to the rotation of the anvil roller 15a, ultrasonic vibration energy is supplied to both the sheets 8a and 9a from the vibrating surface 15hs of the horn 15h. Thus, both the sheets 8a and 9a partially generate heat to be melted, so that both the sheets 8a and 9a are joined to produce the exterior sheet 7a in the joining pattern in which a plurality of joined parts j, j . . . (FIG. 4) is non-continuously distributed, as described above. Then, the anvil roller 15a sends out the exterior sheet 7a downstream in the MD direction, thereby allowing the sent-out exterior sheet 7a to be transported to the leg-surrounding opening portion forming processing section 20 located downstream in the MD direction at the transport speed V8a9a that is almost the same value as the peripheral speed V15a.

Figure 7:
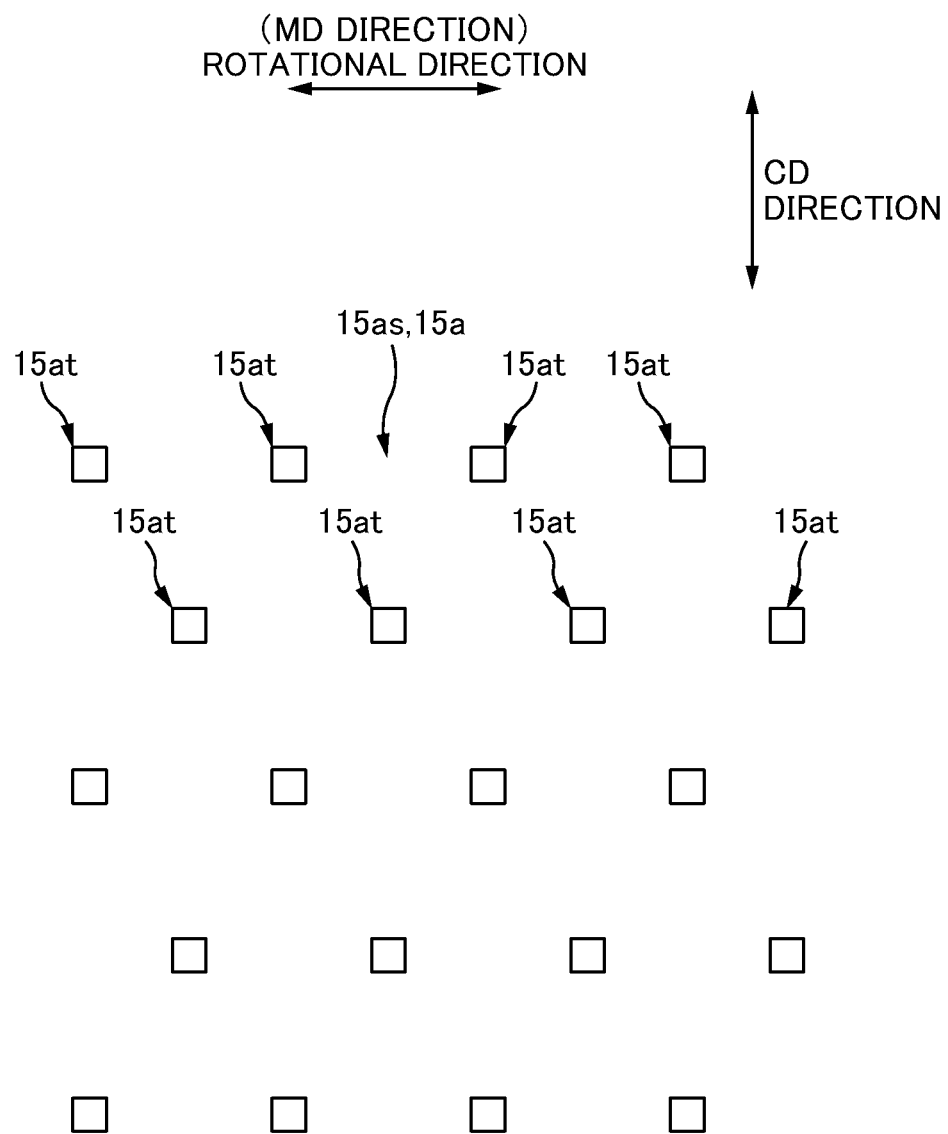
FIG. 7 is a schematic enlarged view illustrating an outer peripheral surface 15$as$ of an anvil roller 15$a$ in a developed state in the rotational direction.

FIG. 7 is a schematic enlarged view illustrating the outer peripheral surface 15as of the anvil roller 15a by developing it in the rotational direction. As illustrated in FIG. 7, a plurality of protrusions 15at, 15at . . . is arranged on the outer peripheral surface 15as of the anvil roller 15a in a staggered pattern as an arrangement pattern corresponding to the joining pattern described above in order to form the joined parts j, j . . . in the joining pattern described above.

Note that, in this example, as illustrated in FIG. 7, a square is exemplified as a planar shape of the top surface of each of the protrusions 15at of the anvil roller 15a. However, the shape is not limited thereto. For example, a regular polygon that is a regular pentagonal shape or more may be used, a perfectly circular shape may be used, and the shape other than these shapes may be used.

Further, respective sizes in the CD direction and the MD direction of the top surface of each of protrusions 15at are selected, for example, from a range of 0.1 mm to 4 mm, respectively, and preferably, selected from a range of 0.2 mm to 2 mm. In this way, it is possible to prevent the each of the protrusions 15*at* from penetrating both the sheets 8*a* and 9*a* and causing poor joining, and to effectively prevent both the sheets 8*a* and 9*a* from hardening due to the increase of the area of the each joined part j. Further, the protrusion height of the top surface of each of the protrusions 15*at* is selected from, for example, a range of 1.0 mm to 3 mm, and preferably, selected from a range of 1.2 mm to 1.8 mm.

Meanwhile, the vibrating surface 15*hs* of the horn 15*h* has a rectangular plane shape that is long in the CD direction, and the vibrating direction thereof is defined as a normal direction. The surface 15*hs* is sized in the CD direction so as to protrude on both sides in the CD direction from the smaller of the sheets 8*a* and 9*a*. Further, the surface 15*hs* is sized in the MD direction such that the surface 15*hs* protrudes to the both sides in the MD direction from the top surface of the protrusion 15*at* of the anvil roller 15*a*, and is preferably sized such that the surface 15*hs* protrudes on the both sides in the MD direction from the top surfaces of the plurality of protrusions 15*at*, 15*at* . . . arranged in the MD direction. In this example, the surface 15*hs* is sized so as to protrude on the both sides in the MD direction from the top surfaces corresponding to ten protrusions 15*at*, 15*at* . . . arranged in the MD direction. Accordingly, the area of the vibrating surface 15*hs* is sufficiently larger than the area of the top surface of the protrusion 15*at*.

Thus, the portions of both the sheets 8*a* and 9*a*, which are opposed to the top surface of each of the protrusions 15*at* described above, are selectively sandwiched and pressed by the vibrating surface 15*hs* of the horn 15*h*, and thus ultrasonic vibration energy is supplied to the portions stated above to melt them. Accordingly, the joined parts j, j . . . are formed in the portions opposing the top surfaces of the respective protrusions 15*at*.

Incidentally, in the ultrasonic welding device 15 associated with the present embodiment, an arrangement relation of the horn 15*h* and the anvil roller 15*a* is devised with respect to both sheets 8*a* and 9*a* for the purpose of solving the problem of strength reduction of the joined part j that is the fixing part j of both the sheets 8*a* and 9*a* described above. In other words, as illustrated in FIG. 6A, at the arrangement position P15*h* of the horn 15*h* described above, in which both the sheets 8*a* and 9*a* are to be sandwiched by the horn 15*h* and the anvil roller 15*a*, the low-stretchable sheet 9*a* is configured so as to be located between the elastic sheet 8*a* and the top surface of each of the protrusions 15*at* of the anvil roller 15*a* as illustrated in FIG. 6B. More specifically, each of the protrusions 15*at* of the outer peripheral surface 15*as* of the anvil roller 15*a* is arranged on the low-stretchable sheet 9*a* side, and also the vibrating surface 15*hs* of the horn 15 is arranged on the elastic sheet 8*a* side.

In this way, as illustrated in FIG. 6B, each of the protrusions 15*at* of the anvil roller 15*a* presses the elastic sheet 8*a* via the low-stretchable sheet 9*a*. Thus, the low-stretchable sheet 9*a* becomes a shock-absorbing material, so that it is possible to effectively prevent a situation where the elastic sheet 8*a* is locally thinly stretched. In particular, in this example, since the elastic sheet 8*a* is nonwoven fabric, each fiber is stretched and easily escapes from the top surface of each of the protrusions 15*at*, and each fiber is less likely to remain on the top surface. However, in this regard, the low-stretchable sheet 9*a* comes into contact with the top surface in this device 15, and thus the escape of each fiber of the elastic sheet 8*a* described above can be effectively prevented.

Further, the area of the flat vibrating surface 15*hs* described above that presses the elastic sheet 8*a* not via the low-stretchable sheet 9*a* is sufficiently larger than the area of the top surface of the aforementioned protrusion 15*at* as described above. Thus, there is almost no case where the elastic sheet 8*a* is locally thinly stretched due to the press of the vibrating surface 15*hs*. Accordingly, sufficient amount of the elastic sheet 8*a* can remain on the top surface of the protrusion 15*at*.

On the other hand, the low-stretchable sheet 9*a* located on the protrusion 15*at* side relative to the elastic sheet 8*a* has lower elasticity than that of the elastic sheet 8*a*. Thus, it is possible to effectively prevent a situation where the low-stretchable sheet 9*a* is locally thinly stretched due to the press of the top surface of the protrusion 15*at* on the basis of the low stretchability of the sheet 9*a* itself, enabling the sufficient amount of the low-stretchable sheet 9*a* to remain on the top surface of the protrusion 15*at*. Consequently, strength of the joined part j of the low-stretchable sheet 9*a* and the elastic sheet 8*a* can be ensured, that is, strength reduction of the joined part j of both the sheets 8*a* and 9*a* can be suppressed.

Note that, in this example, as illustrated in FIG. 6A, both the sheets 8*a* and 9*a* are allowed to wrap around the protrusions 15*at* of the outer peripheral surface 15*as* of the anvil roller 15*a*, and thus the transport path of both the sheets 8*a* and 9*a* is formed into an arc shaped along the outer peripheral surface 15*as*. Also, the transport path includes the arrangement position P15*h* of the horn 15*h* described above. That is, both the sheets 8*a* and 9*a* wrap around the protrusions 15*at* of the outer peripheral surface 15*as* of the anvil roller 15*a* not only on the upstream side but also on the downstream side from the position P15*h* in the rotational direction (MD direction). Thus, the transport state of both the sheets 8*a* and 9*a* can be stabilized also at the arrangement position P15*h* of the horn 15*h*, thereby enabling both the sheets 8*a* and 9*a* to be accurately and firmly joined at the position P15*h*.

Incidentally, since when the peripheral speed V15*a* of the anvil roller 15*a* fluctuates, the time (second) required for both the sheets 8*a* and 9*a* to pass through the arrangement position P15*h* of the horn 15*h* also fluctuates, the ultrasonic vibration energy (J) supplied to both the sheets 8*a* and 9*a* also fluctuates. For example, when the peripheral speed V15*a* is increased, the ultrasonic vibration energy (J) to be supplied is decreased, whereas when the peripheral speed V15*a* is decreased, the ultrasonic vibration energy (J) to be supplied is increased. Accordingly, the joining strength of the joined part j may fluctuate accompanying the fluctuation of the peripheral speed V15*a*.

In this example, as illustrated in FIG. 6A, a pressing force F (N) in the direction toward the outer peripheral surface 15*as* of the anvil roller 15*a* is exerted to the horn 15*h* for the purpose of suppressing the fluctuation of the joining strength, and the pressing force F (N) is increased or decreased in conjunction with the increase or decrease of the peripheral speed V15*a* of the anvil roller 15*a*. The details are as follows.

First, the horn 15*h* is supported by the aforementioned support member 16*s* via an appropriate actuator 16 such as an air cylinder and a hydraulic cylinder. Further, on the basis of the peripheral speed V15*a* (m/min) of the anvil roller 15*a* which is measured by an appropriate sensor (not shown) such as encoder, an appropriate controller (not shown) such as a computer controls the aforementioned actuator 16*a*. For example, when the peripheral speed V15*a* of the anvil roller 15*a* is increased, the pressing force F is increased, whereas when the peripheral speed V15*a* is decreased, the pressing force F is decreased. Then, when the pressing force F is increased, the ultrasonic vibration energy (J) to be supplied is increased, on the other hand, when the pressing force F is decreased, the ultrasonic vibration energy (j) to be supplied is decrease. Thus, when the pressing force F is increased or decreased in conjunction with the increase or decrease of the peripheral speed V15a as described above, the fluctuation of the supply amount (J) of the ultrasonic vibration energy due to the increase or decrease of the peripheral speed V15a can be reduced, and thus the joining strength of the joined part j can be substantially uniformly maintained without depending on the fluctuation of the peripheral speed V15a of the anvil roller 15a.

Figure 8A:
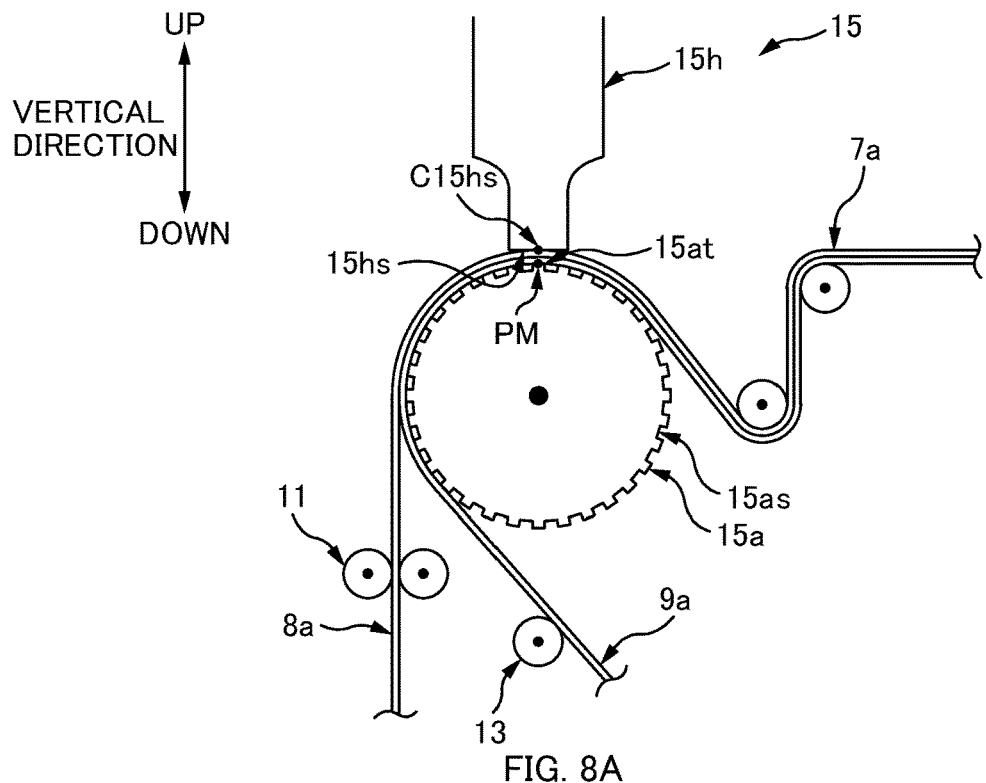
FIG. 8A and FIG. 8B are explanatory diagrams of the comparative example of a position adjusting method of the horn 15$h$ and the anvil roller 15$a$, and are schematic enlarged side views of the ultrasonic welding device 15.

Incidentally, as a method of adjusting positions of the horn 15h and the anvil roller 15a, for example, the following method can be considered. That is, it is considered that, while the anvil roller 15a is not rotating as shown in FIG. 8A, the position of the horn 15h is adjusted so that a contact position PM in which a tangent line parallel to the vibrating surface 15hs contacts the top surface of each of the protrusions 15at of the outer peripheral surface 15as of the anvil roller 15a conforms to the center position C15hs of the vibrating surface 15hs.

Figure 8B:
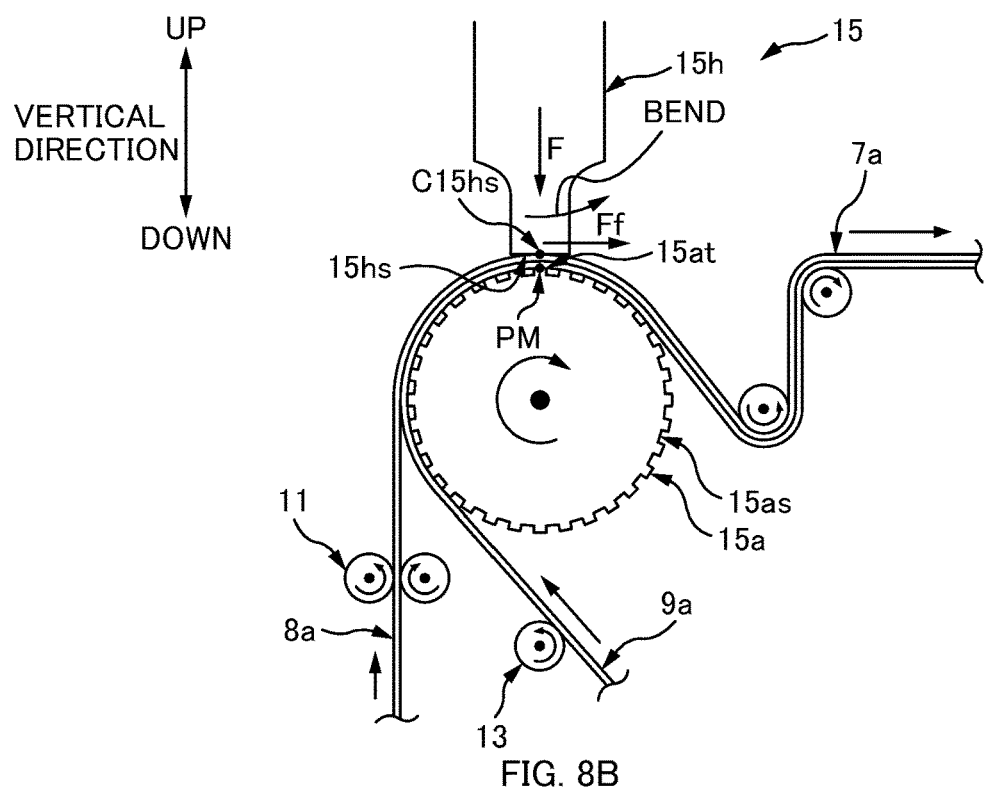

However, at the time of rotation of the anvil roller 15a, since the horn 15h is slightly bent to the downstream side in the rotational direction (MD direction) due to a sliding force Ff exerted from the rotating anvil roller 15a through the vibrating surface 15h as illustrated in FIG. 8B, the vibrating surface 15hs slightly inclines corresponding to the amount of bending while moving to the downstream side in the rotational direction, thereby narrowing the space between the vibrating surface 15hs and each of the protrusions 15at of the outer peripheral surface 15as of the anvil roller 15a. Thus, the vibrating surface 15hs may be caught by each of the protrusions 15at.

Figure 9:
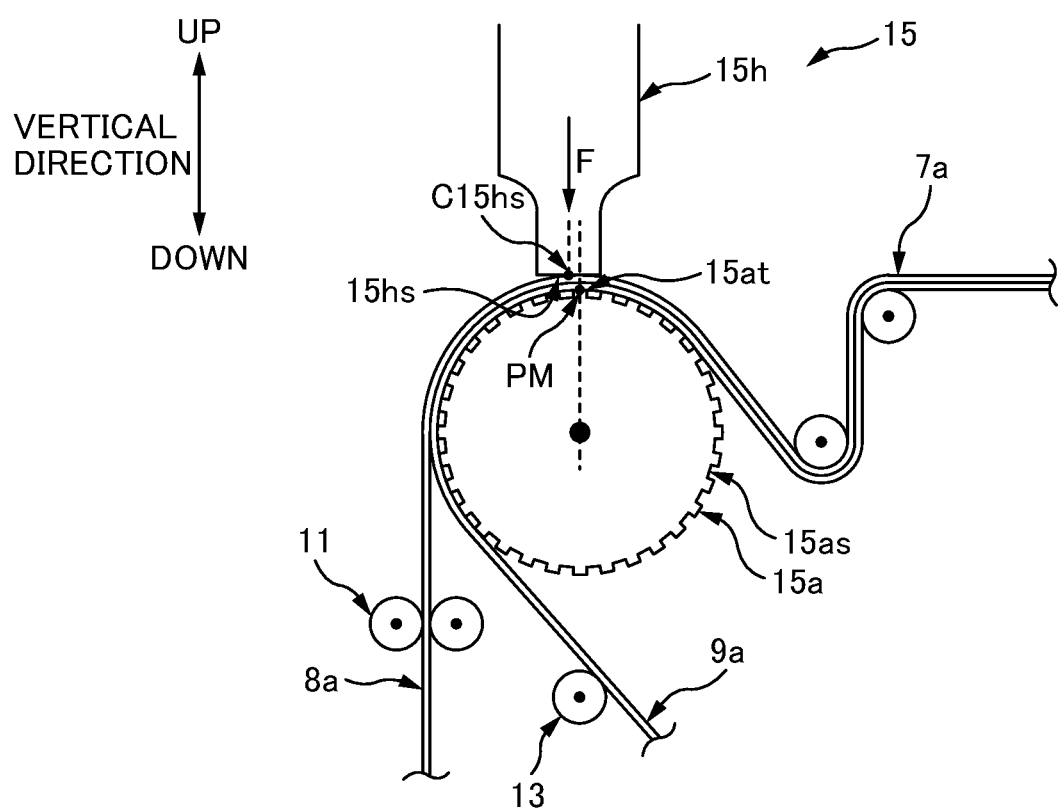
FIG. 9 is an explanatory diagram of an example of the position adjusting method of the horn 15$h$ and the anvil roller 15$a$, and is a schematic enlarged side view of the ultrasonic welding device 15.

Accordingly, in this example, the following position adjustment is performed in order to prevent the vibrating surface 15hs from being caught. That is, as illustrated in FIG. 9, in a non-rotating state of the anvil roller 15a, the position of the horn 15h is adjusted so that the center position C15hs of the vibrating surface 15hs is located on the upstream side in the rotational direction (MD direction) relative to the contact position PM described above. Thus, even if the horn 15h is pressed by the rotating anvil roller 15a and the horn 15h slightly bends, the space between the vibrating surface 15hs and each of the protrusions 15at can be widely secured by the amount in which the center position C15hs of the vibrating surface 15hs is located on the upstream side relative to the aforementioned contact position PM, as stated above. Consequently, it is possible to effectively suppress that the vibrating surface 15hs is caught by each of the protrusions 15at.

In the description stated above, it is described that "the low-stretchable sheet 9a is in a strained state", and in such a strained state, the low-stretchable sheet 9a is in a so-called fully stretched-out state that is a state in which the sheet hardly stretches any more due to its low stretchability. Accordingly, even if unexpected tensile force is exerted during the subsequent transportation, it is possible to resist the tensile force described above with the low-stretchable sheet 9a so as not to change the length of the exterior sheet 7a in the MD direction. Incidentally, if the "fully stretched-out state" is defined, for example, it can be defined as "a state in which the sheet is not broken while the state of the sheet is maintained, and a state in which the sheet is not to be further stretched at a stretch rate of 5% or greater from the present state".

Further, the "stretch magnification" described above indicates how many times the entire length of the elastic sheet 8a in the stretched state is stretching from its natural length before being stretched. Also, the stretch magnification defines how much the exterior sheet 7 (7a) of the completed diaper 1 can stretch in the width direction from an unloaded state. That is, in the diaper 1 manufactured by setting the elastic sheet 8a in a predetermined stretch magnification, the exterior sheet 7 (7a) can stretch in the width direction of the diaper 1 up to the stretched state corresponding to this stretch magnification. This stretch magnification is set, for example, to an arbitrary value in a rage of 1.5 to 4 times, and in this example, the stretch magnification is set to 2.5 times.

Then, the exterior sheet 7a produced in the exterior sheet generation processing section 10 in this manner is transported downstream in the MD direction as illustrated in FIG. 5A and FIG. 5B. When the exterior sheet 7a passes through each of the processing sections 20 to 60 located downstream thereof, respective processing is performed at each of the processing sections 20 to 60. Note that, each of the processing sections 20 to 60 can be configured by respectively using well-known devices. Thus, brief explanation will be given below.

As illustrated in FIG. 5A, the leg-surrounding opening portion forming processing section 20 includes a well-known die cutter device 21. The leg-surrounding opening portion 7HL is punched by the device 21 at a predetermined pitch in the MD direction with respect to the exterior sheet 7a to be transported in the MD direction.

The next absorbent main body attachment processing section 30 includes a well-known rotary drum device 31. In the device 31, the absorbent main body 3 is attached to the exterior sheet 7a at a predetermined pitch in the MD direction. That is, the absorbent main body 3 is attached to the exterior sheet 7a at a position between the adjacent leg-surrounding opening portions 7HL, 7HL in the MD direction.

The next twofold processing section 40 includes a well-known guide member (not shown). When passing through a position of the guide member, the exterior sheet 7a to which the absorbent main body 3 has been attached is folded in two in the CD direction with a substantially center part in the CD direction corresponding to the crotch part 7c of the diaper 1 as a folding position, thereby allowing one end portion and the other end portion of the exterior sheet 7a in the CD direction to be superposed in the thickness direction.

The next end seal processing section 50 includes a well-known heat sealing processing device 51. The one end portion and the other end portion of the exterior sheet 7a in the CD direction, which are superposed in the thickness direction by being folded in two, are welded by the device 51 at the position between the adjacent absorbent main bodies 3, 3 in the MD direction to fix them in the two-folded state. Note that, the welded portions remain on the exterior sheet 7a as the end seal parts jes described above.

The final separation processing section 60 includes a well-known rotary cutter device 61. The device 61 divides the exterior sheet 7a fixed in the two-folded state at a predetermined pitch, thereby separating the downstream end portion from the exterior sheet 7a at the position of the aforementioned end seal parts jes and producing the diaper 1. Then, each of the produced diapers 1 is sent downstream in the MD direction by an appropriate transport mechanism CV such as a belt conveyor.

Other Embodiments

While the embodiment of the present invention has been described above, the above embodiment has been presented for easy understanding of the present invention and not for construing the invention in a limited way. And it is needless to say that the present invention can be changed and improved without departing from the gist of the invention, and includes equivalents thereof. For example, modifications as described below are possible.

In the embodiment described above, the staggered pattern is exemplified as an arrangement pattern of the joined parts j, j . . . , as illustrated in FIG. 4. However, the arrangement pattern is not limited thereto. For example, a grid pattern in which the joined parts j, j . . . are respectively formed on intersection points of grids may be employed, and a pattern other than that may be employed.

Figure 10A:
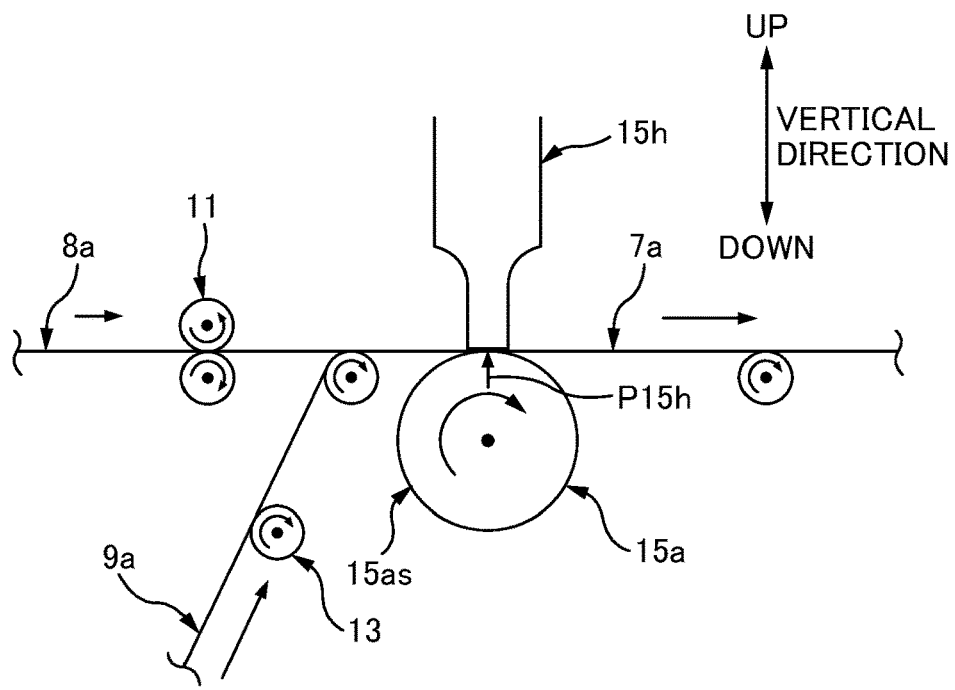
FIG. 10A and FIG. 10B are respectively schematic side views of an ultrasonic welding device 15 in the other embodiments.
Figure 10B:
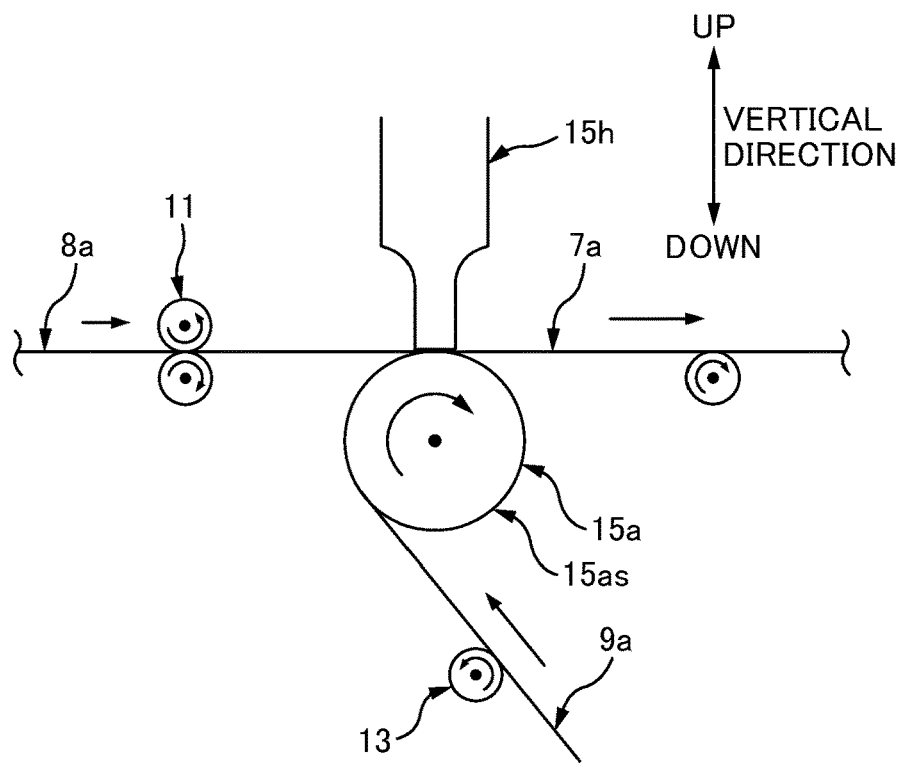

In the embodiment described above, as illustrated in FIG. 6A, both the elastic sheet 8a and the low-stretchable sheet 9a are wrapped around the protrusions 15at of the outer peripheral surface 15as of the anvil roller 15a over a predetermined range in the rotational direction, thereby transporting these both sheets 8a and 9a along the transport path that curves in an arc shape along the outer peripheral surface 15as of the anvil roller 15a. Although the transport path includes the arrangement position P15h of the horn 15h, the invention is not limited thereto. In other words, as illustrated in FIG. 10A, while both the sheets 8a and 9a are transported along a linear transport path in a state in which both the sheets 8a and 9a are superposed in the thickness direction, the transport path may include the aforementioned arrangement position P15h, or, as illustrated in FIG. 10B, while the elastic sheet 8a is transported along the linear transport path, only the low-stretchable sheet 9a may be transported by being wrapped around the protrusions 15at of the outer peripheral surface 15as of the anvil roller 15a. However, as illustrated in FIG. 6A and FIG. 10B, if each of the sheets 8a and 9a is wrapped around the protrusions 15at of the outer peripheral surface 15as of the anvil roller 15a, the transport state of each of the sheets 8a and 9a can be stabilized. This leads to accurate and firm fixation of both the sheets 8a and 9a. Thus, wrapping around the protrusions is preferable.

Figure 11A:
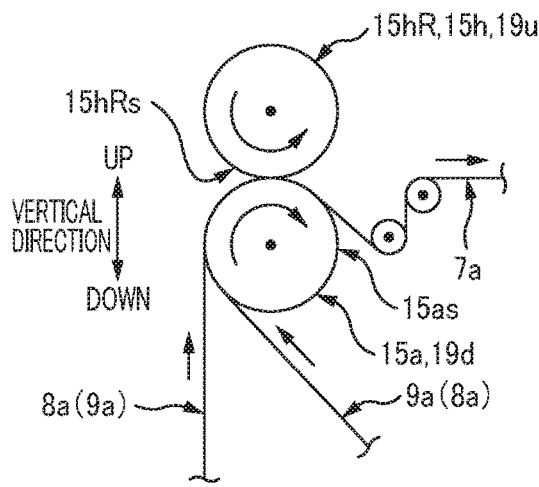
FIG. 11A to FIG. 11F are respectively schematic side views of the ultrasonic welding device 15 in the other embodiments.

In the embodiment described above, as illustrated in FIG. 6A, the horn 15h of the ultrasonic welding device 15 is substantially unmovably and unrotatably configured, and also its vibrating surface 15hs is a rectangular planar surface. However, the invention is not limited thereto. For example, the horn 15h may also have the same roller configuration as the anvil roller 15a, as illustrated in FIG. 11A.

In more detail, the horn 15h is configured as a roller 15hR (hereinafter, referred to as a horn roller 15hR, and corresponding to the "second rotating member") that can rotate around the rotary shaft along the CD direction, and its outer peripheral surface 15hRs may also functions as a vibrating surface. Note that, in this case, the outer peripheral surface 15hRs of the horn roller 15hR, which is the vibrating surface, vibrates in a direction in which the space between the outer peripheral surface 15as of the anvil roller 15a and the outer peripheral surface 15hRs is expanded or contracted, for example, in an up-down direction in FIG. 11A. Further, a plurality of protrusions 15at, 15at . . . (not shown in FIG. 11A) described above is provided on the outer peripheral surface 15as (or 15hRs) of the one roller 15a (or 15hR) of the anvil roller 15a and the horn roller 15hR in FIG. 11A, whereas the other roller 15hR (or 15a) includes the smooth outer peripheral surface 15hRs (or 15as) without the protrusions 15at, 15at . . . thereon. Then, the low-stretchable sheet 9a is arranged on the roller 15a (15hR) side having the outer peripheral surface 15as (15hRs) that includes the former protrusions 15at, and the elastic sheet 8a is arranged on the roller 15hR (15a) side having the latter smooth outer peripheral surface 15hRs (15as).

Figure 11B:
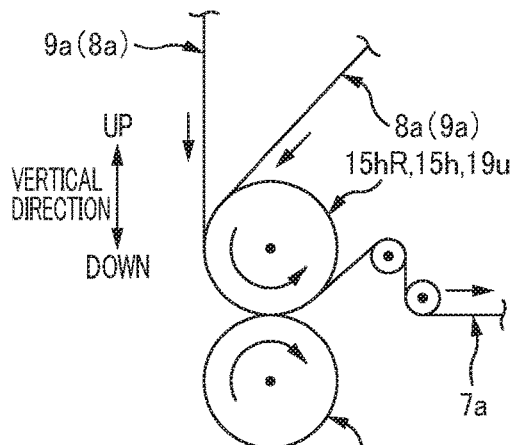
Figure 11C:
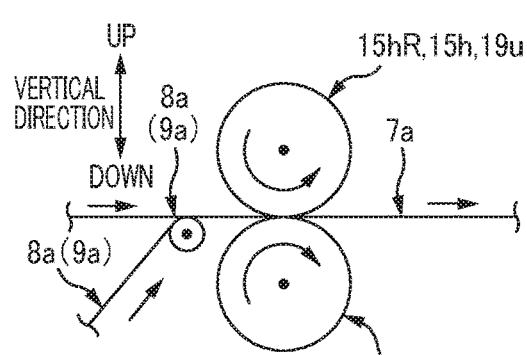
Figure 11D:
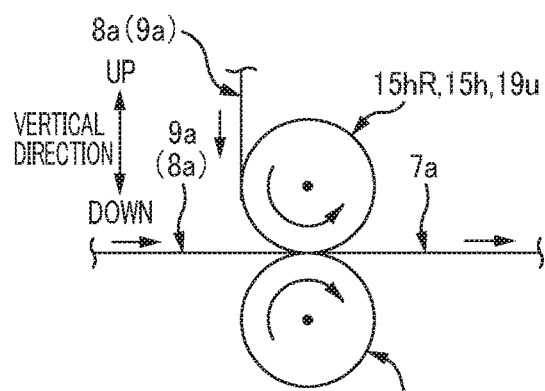
Figure 11E:
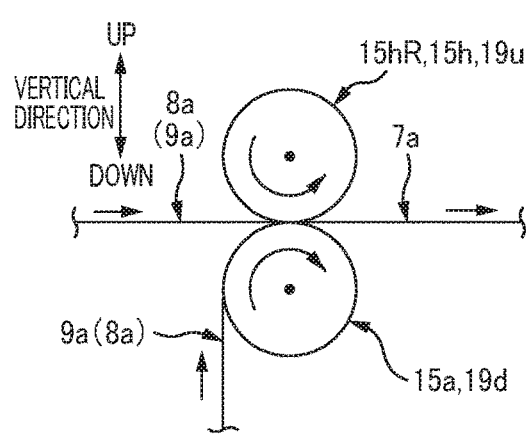
Figure 11F:
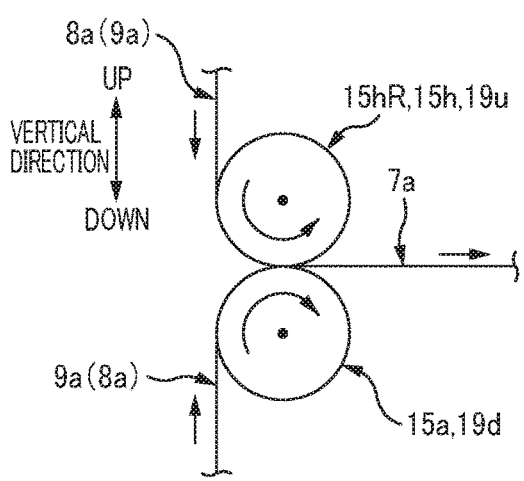

Further, in the case that the horn roller 15hR stated above is included, both the sheets 8a and 9a may be wrapped around the horn roller 15hR as illustrated in FIG. 11B, and both the sheets 8a and 9a may be transported along the linear transport path without being wrapped around both the horn roller 15hR and the anvil roller 15a as illustrated in FIG. 11C. Moreover, as illustrate in FIG. 11D, the one sheet 8a (9a) of both sheets 8a and 9a is wrapped around the horn roller 15hR, whereas the other sheet 9a (8a) may be transported along the linear transport path without being wrapped around either rollers 15hR and 15a, and vice versa. In other words, as illustrated in FIG. 11E, the one sheet 9a (8a) of both the sheets 8a and 9a is wrapped around the anvil roller 15a, whereas the other sheet 8a (9a) may be transported along the linear transport path without being wrapped around either rollers 15a or 15hR. Furthermore, as illustrated in FIG. 11F, the one sheet 8a (9a) of both the sheets 8a and 9a is wrapped around the horn roller 15hR, whereas the other sheet 9a (8a) may be wrapped around the anvil roller 15a. However, the roller 15a (15hR) having the outer peripheral surface 15as (15hRs) including the protrusions 15at can hold the low-stretchable sheet 9a on its outer peripheral surface 15as (15hRs) with a high holding property due to the protrusions 15at, 15at . . . . Accordingly, a case in which the low-stretchable sheet 9a is transported while being wrapped around the roller 15a (15hR) that has the protrusions 15at is more preferable to stabilize the transport state of the sheet 9a, rather than a case in which the low-stretchable sheet 9a is transported along the linear transport path.

In the embodiment described above, as illustrated in FIG. 6A, the joining of the elastic sheet 8a and the low-stretchable sheet 9a, which is executed in the exterior sheet generation processing section 10, is performed by the ultrasonic welding device 15. However, the invention is not limited thereto. For example, a heat sealing processing device or a pressure bonding device may be used instead of the ultrasonic welding device 15. Note that, the structure of the heat sealing processing device and the structure of the pressure bonding device are similar to each other. In other words, a difference between both structures is mainly only that the roll is heated or not, and both devices include a pair of upper and lower rolls 19u, 19d that is driven to rotate around the rotary shaft along the CD direction. Further, when the devices are illustrated when seen from the side, it becomes similar to the aforementioned structures illustrated in FIG. 11A to FIG. 11F, that is, the structure including the horn roller 15hR and the anvil roller 15a. Thus, the following description is given by alternatively using these FIG. 11A to FIG. 11F.

As illustrated in FIG. 11A to FIG. 11F, a plurality of protrusions (not shown) is arranged on the outer peripheral surface of the one roll 19u (19d) of the pair of upper and lower rolls 19u, 19d in an arrangement pattern corresponding to the aforementioned joining pattern, whereas the outer peripheral surface of the other roll 19d (19u) is a smooth surface. The low-stretchable sheet 9a is arranged on the roll 19u (19d) side having the outer peripheral surface including the former protrusions, and the elastic sheet 8a is arranged on the roll 19d (19u) side having the latter smooth outer peripheral surface. Further, each of these rolls 19u, 19d is configured so as to rotate at the same peripheral speed as the peripheral speed V15a of the anvil roller 15a in the case of the aforementioned ultrasonic welding device 15. Thus, when both the sheets 8a and 9a pass through a roll gap between the rolls 19u, 19d in the state of being superposed with each other, both the sheets 8a and 9a are sandwiched and pressed by each of the protrusions of the one roll 19u (19d) and the smooth outer peripheral surface of the other roll 19d (19u), and thus welding parts or press-bonding parts are formed in both sheets 8a and 9a as the joined parts j, j . . . associated with the aforementioned joining pattern.

Figure 12:
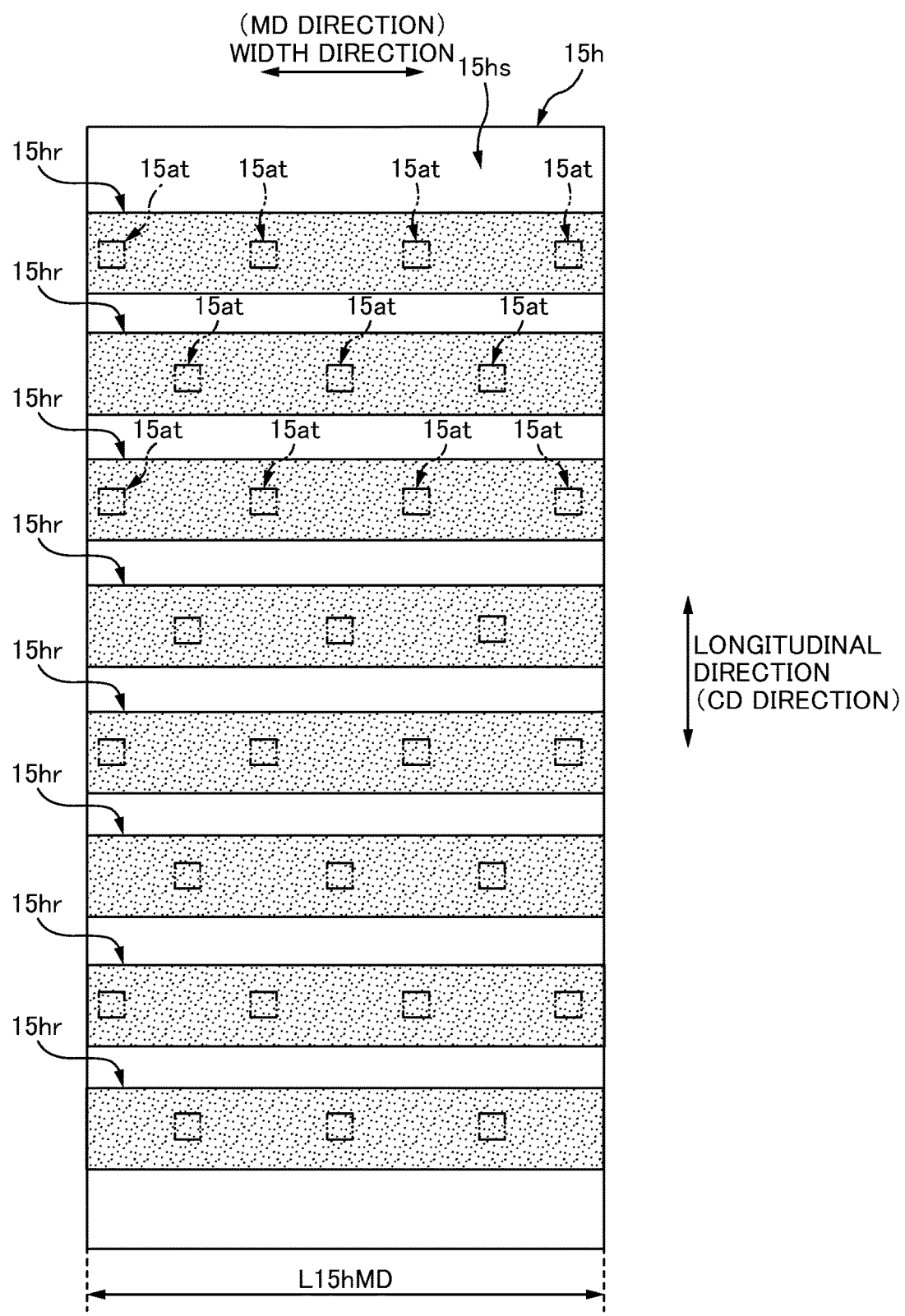
FIG. 12 is a schematic view of a vibrating surface 15$hs$ in which rib portions 15$hr$, 15$hr$ . . . as a surface portion are provided at a position opposing each of protrusions 15$at$ of the anvil roller 15$a$.

In the embodiment described above, the horn 15*h* is exemplified as a sandwiching member, and also the flat vibrating surface 15*hs* of the horn 15*h* is exemplified as a surface portion that is larger than the protrusion 15*at*. However, the invention is not limited thereto. In other words, if the area of the surface portion is larger than the area of the top surface of the protrusion 15*at*, an effect of suppressing strength reduction of the aforementioned joined part j can be properly obtained. Thus, the surface portion is not limited to a flat surface over the substantially entire surface, such as the vibrating surface 15*hs* of the FIG. 6A described above. FIG. 12 is an explanatory diagram of an example thereof, and a view in which the vibrating surface 15*hs* of the horn 15*h* is seen from the normal direction. Note that, in FIG. 12, although the protrusions 15*at* of the anvil roller 15*a* are also virtually illustrated together by double-dotted chained lines, these protrusions 15*at* are not in a static state as shown in FIG. 12, that is, move sequentially to the MD direction in conjunction with the rotating motion of the anvil roller 15*a*.

AS illustrated in FIG. 12, in this example, the vibrating surface 15*hs* of the horn 15*h* includes a plurality of rib portions 15*hr*, 15*hr* . . . as the aforementioned surface portion. Each of the rib portions 15*hr* is provided at a position that is opposed to each of the protrusions 15*at* of the anvil roller 15*a*, protrudes in the normal direction of the vibrating surface 15*hs* and extends in a band shape along the MD direction. Further, the top surface of each of the rib portions 15*hr* is a flat surface over the substantially entire surface, and the top surface in the CD direction is sized such that each of the protrusions 15*at* does not protrude to the both sides in the CD direction from the top surface (portions shown by the dot pattern in FIG. 12) of the rib portion 15*hr* while each of the protrusions 15*at* are moving on the entire length L15*h*MD of the horn 15*h* along the MD direction. For example, in this example, the dimension of the rib portion 15*hr* in the CD direction is three times as large as the dimension of the protrusion 15*at* in the CD direction. Thus, in a case in which the top surface of the rib portion 15*hr* comes into contact with the elastic sheet 8*a* rather than a case in which the top surface of each of the protrusions 15*at* comes into contact with the elastic sheet 8*a*, it is possible to prevent the elastic sheet 8*a* from being thinly stretched, thereby suppressing strength reduction of each joined part j.

In the embodiment described above, the elastic sheet 8*a* is fixed to the low-stretchable sheet 9*a* in the exterior sheet generation processing section 10. However, a different sheet or a plurality of different sheets may be further added and fixed. Note that, as a sheet to be added and fixed, an elastic sheet may be used, or a low-stretchable sheet may be used. Further, the form of the sheet may be nonwoven fabric, or woven fabric, or a film. Furthermore, the sheet to be added may be interposed between the elastic sheet 8*a* and the low-stretchable sheet 9*a*, or may be fixed on the elastic sheet 8*a* side, or may be fixed on the low-stretchable sheet 9*a* side.

REFERENCE SIGNS LIST

1: disposable diaper (absorbent article),
3: absorbent main body, 3*e*: end portion,
4: top sheet, 4*e*L: projected portion,
5: leak-proof sheet, 5*e*L: projected portion, 5*e*W: projected portion,
7: exterior sheet, 7HL: leg-surrounding opening portion.
7*f*: abdomen side part, 7*b*: back side part, 7*c*: crotch part, 7*e*W: end portion,
7*a*: continuous sheet of exterior sheet (exterior sheet, base material sheet),
8: inner layer sheet (elastic sheet),
8*a*: continuous sheet of elastic sheet (elastic sheet),
9: outer layer sheet (low-stretchable sheet),
9*a*: continuous sheet of low-stretchable sheet (low-stretchable sheet),
10: exterior sheet generation processing section,
11: transport mechanism (nip roll mechanism), 11R: nip roll,
13: transport mechanism, 13R: transport roller,
15: ultrasonic welding device (fixing device),
15*a*: anvil roller (rotating member), 15*as*: outer peripheral surface,
15*h*: horn (sandwiching member), 15*h*R: horn roller (second rotating member),
15*h*Rs: outer peripheral surface,
15*hs*: vibrating surface (surface portion),
15*hr*: rib portion,
16*a*: actuator, 16*s*: support member,
19*u*: upper roll, 19*d*: lower roll,
20: leg-surrounding opening portion forming processing section, 21: die cutter device,
30: absorbent main body attachment processing section, 31: rotary drum device,
40: twofold processing section,
50: end seal processing section, 51: heat sealing processing device,
60: separation processing section, 61: rotary cutter device,
HB: waist opening portion, HL: leg-surrounding opening portion,
CV: transport mechanism,
LM: manufacturing line,
PM: contact position, C15*hs*: center position, P15*h*: arrangement position (predetermined position),
j: joined part (welding part, fixing part), Rj: joined part line,
j3: joined part, j3L: longitudinal band-like portion, j3W: laterally long band-like portion, j3C: joined part,
jn: non-joined part, F: pressing force, Ff: sliding force,
jes: end seal part.

The invention claimed is:

1. A fixing device for fixing a plurality of sheets associated with an absorbent article, the plurality of sheets including an elastic sheet and a low-stretchable sheet that has lower stretchability than that of the elastic sheet, the fixing device comprising:
   a rotating member that has an outer peripheral surface and includes a plurality of protrusions on the outer peripheral surface, the rotating member configured to rotate along a transport direction in which the elastic sheet is transported; and
   a sandwiching member that is arranged at a predetermined position in a rotational direction of the rotating member, and configured to sandwich the elastic sheet and the low-stretchable sheet by a surface portion of the sandwiching member in cooperation with each of the protrusions when each of the protrusions passes through the predetermined position, the surface portion, which contacts the elastic sheet, being larger than a top surface of each of the protrusions,
   wherein
   the sandwiching member and the rotating member are configured to cooperatively sandwich the elastic sheet and the low-stretchable sheet at a sandwiching position in which the low-stretchable sheet is located between the elastic sheet and the top surface of each of the protrusions of the rotating member, to form a plurality of fixing parts where the elastic sheet is fixed to the low-stretchable sheet, the fixing device is configured to cause the low-stretchable sheet to be wrapped around the rotating member and to be transported to the sandwiching position in a strained state between the protrusions, the sandwiching member is unrotatable and provided along the transport direction, the sandwiching member is configured to receive a pressing force in a direction toward the outer peripheral surface of the rotating member, the surface portion of the sandwiching member includes a flat surface opposing the outer peripheral surface of the rotating member, and in a non-rotating state of the rotating member, a center position of the flat surface of the surface portion is located at an upstream side position in the transport direction with respect to a contact position in which a tangent line parallel to the flat surface of the surface portion contacts each of the protrusions on the outer peripheral surface of the rotating member.

2. The fixing device according to claim 1, wherein
the fixing device is configured to cause the low-stretchable sheet to be wrapped around the protrusion of the outer peripheral surface over a predetermined range of the rotating member in the rotational direction so as to be transported along a transport path that curves in an arc shape along the outer peripheral surface of the rotating member, and the surface portion of the sandwiching member is arranged opposing the outer peripheral surface at the predetermined position included in the predetermined range.

3. The fixing device according to claim 2, wherein
the fixing device is configured to cause the elastic sheet to be wrapped around the protrusion of the outer peripheral surface by being superposed from above the low-stretchable sheet that is wrapped around the protrusion of the outer peripheral surface of the rotating member.

4. The fixing device according to claim 1, wherein
the surface portion of the sandwiching member is configured to vibrate at a frequency corresponding to ultrasound in a direction in which a space between the outer peripheral surface of the rotating member and the surface portion of the sandwiching member is expanded or contracted.

5. A method of fixing a plurality of sheets associated with an absorbent article, the plurality of sheets including an elastic sheet and a low-stretchable sheet that has lower stretchability than that of the elastic sheet, the method comprising:

rotating, along a transport direction in which the elastic sheet is transported, a rotating member that has an outer peripheral surface and includes a plurality of protrusions on an outer peripheral surface;

arranging a sandwiching member at a predetermined position in a rotational direction of the rotating member, the sandwiching member including a surface portion larger than a top surface of each of the protrusions; and sandwiching the elastic sheet and the low-stretchable sheet cooperatively by each of the protrusions and the surface portion of the sandwich member when each of the protrusions passes through the predetermined position, to form a plurality of fixing parts where the elastic sheet is fixed to the low-stretchable sheet;

wherein
the sandwiching member and the rotating member cooperatively sandwich the elastic sheet and the low-stretchable sheet at a sandwiching position in which the low-stretchable sheet is located between the elastic sheet and the top surface of each of the protrusions of the rotating member, the low-stretchable sheet is wrapped around the rotating member and is transported to the sandwiching position in a strained state between the protrusions, the sandwiching member is unrotatable and provided along the transport direction, the sandwiching member receives a pressing force in a direction toward the outer peripheral surface of the rotating member, the surface portion of the sandwiching member includes a flat surface opposing the outer peripheral surface of the rotating member, and in a non-rotating state of the rotating member, a center position of the flat surface of the surface portion is located at an upstream side position in the transport direction with respect to a contact position in which a tangent line parallel to the flat surface of the surface portion contacts each of the protrusions on the outer peripheral surface of the rotating member.

6. A fixing device for fixing a plurality of sheets associated with an absorbent article, the plurality of sheets including an elastic sheet and a low-stretchable sheet that has lower stretchability than that of the elastic sheet, the fixing device comprising:

a rotating member that has an outer peripheral surface and includes a plurality of protrusions on the outer peripheral surface, the rotating member configured to rotate along a transport direction in which the elastic sheet is transported;

a sandwiching member that is arranged at a predetermined position in a rotational direction of the rotating member, and configured to sandwich the elastic sheet and the low-stretchable sheet by a surface portion of the sandwiching member in cooperation with each of the protrusions when each of the protrusions passes through the predetermined position, the surface portion being larger than a top surface of each of the protrusions; and a transport roller configured to transfer the low-stretchable sheet to the rotating member, wherein
the sandwiching member and the rotating member are configured to cooperatively sandwich the elastic sheet and the low-stretchable sheet at a sandwiching position in which the low-stretchable sheet is located between the elastic sheet and the top surface of each of the protrusions of the rotating member, to form a plurality of fixing parts where the elastic sheet is fixed to the low-stretchable sheet, the fixing device is configured to cause the low-stretchable sheet to be wrapped around the rotating member and to be transported to the sandwiching position in a strained state between the protrusions, the sandwiching member is unrotatable and provided along the transport direction, the sandwiching member is configured to receive a pressing force in a direction toward the outer peripheral surface of the rotating member, the surface portion of the sandwiching member includes a flat surface opposing the outer peripheral surface of the rotating member, in a non-rotating state of the rotating member, a center position of the flat surface of the surface portion is located at an upstream side position in the transport direction with respect to a contact position in which a tangent line parallel to the flat surface of the surface portion contacts each of the protrusions on the outer peripheral surface of the rotating member, and the rotating member is configured to rotate to transfer the low-stretchable sheet and the elastic sheet at a transport speed substantially equal to a peripheral speed of the transport roller.

7. The fixing device according to claim 1, wherein the fixing device is configured to cause the low-stretchable sheet to be in the strained state, in which the low-stretchable sheet is not to be further stretched at a stretch rate of 5% or greater from a present state, between the protrusions when the low-stretchable sheet is wrapped around the rotating member and transported to the sandwiching position.

8. The method according to claim 5, wherein the surface portion, which is larger than the top surface of each of the protrusions, contacts the elastic sheet.

9. The method according to claim 5, further comprising:
transferring the low-stretchable sheet to the rotating member by a transport roller; and
transferring the low-stretchable sheet and the elastic sheet by the rotating member at a transport speed substantially equal to a peripheral speed of the transport roller.

\* \* \* \* \*

UNITED STATES PATENT AND TRADEMARK OFFICE
CERTIFICATE OF CORRECTION

PATENT NO. : 10,232,596 B2
APPLICATION NO. : 15/306759
DATED : March 19, 2019
INVENTOR(S) : Hiroki Yamamoto and Yoshihiko Matsumoto It is certified that error appears in the above-identified patent and that said Letters Patent is hereby corrected as shown below:

On the Title Page

Item (*) Notice:
This section should be removed.

Item (45) Date of Patent:
Change "*Mar. 19, 2019" to -- Mar. 19, 2019 --.

Signed and Sealed this
Sixteenth Day of July, 2019

Andrei Iancu
*Director of the United States Patent and Trademark Office*